(12) United States Patent
Peng et al.

(10) Patent No.: US 12,303,660 B1
(45) Date of Patent: May 20, 2025

(54) COLCHICINE HYDROGEL MICRONEEDLE AND PREPARATION METHOD THEREOF

(71) Applicants: ANHUI UNIVERSITY OF CHINESE MEDICINE, Hefei (CN); ANHUI BAICAOJINGYAN PHARMACEUTICAL TECHNOLOGY CO., LTD., Hefei (CN)

(72) Inventors: Can Peng, Hefei (CN); Huanhuan Liu, Hefei (CN); Suping Jiang, Hefei (CN); Jiming Ke, Hefei (CN); Jing Zhang, Hefei (CN); Chijing Zuo, Hefei (CN); Cancan Fang, Hefei (CN); Shuangying Gui, Hefei (CN); Daiyin Peng, Hefei (CN)

(73) Assignees: ANHUI UNIVERSITY OF CHINESE MEDICINE, Hefei (CN); ANHUI BAICAOJINGYAN PHARMACEUTICAL TECHNOLOGY CO., LTD., Hefei (CN)

( * ) Notice: Subject to any disclaimer, the term of this patent is extended or adjusted under 35 U.S.C. 154(b) by 0 days.

(21) Appl. No.: 18/863,666

(22) PCT Filed: Mar. 14, 2023

(86) PCT No.: PCT/CN2023/081347
§ 371 (c)(1),
(2) Date: Nov. 7, 2024

(87) PCT Pub. No.: WO2024/051132
PCT Pub. Date: Mar. 14, 2024

(30) Foreign Application Priority Data

Sep. 5, 2022 (CN) .......................... 202211077519.0

(51) Int. Cl.
A61M 37/00 (2006.01)
B29C 35/08 (2006.01)
(Continued)

(52) U.S. Cl.
CPC ..... *A61M 37/0015* (2013.01); *B29C 35/0805* (2013.01); *B29C 37/006* (2013.01);
(Continued)

(58) Field of Classification Search
CPC ...... A61M 37/0015; A61M 2037/0053; A61M 5/00; B29C 35/0805; B29C 37/006;
(Continued)

(56) References Cited

U.S. PATENT DOCUMENTS 10,537,723 B2 * 1/2020 Nishimura ........... B05D 3/0254
2010/0280457 A1 * 11/2010 Tokumoto ........... B81C 1/00206
604/173
2017/0119707 A1 * 5/2017 Alfaras ................ A61K 31/165

FOREIGN PATENT DOCUMENTS

CN 113133991 A 7/2021
CN 113603826 A 11/2021
(Continued)

OTHER PUBLICATIONS

Zhang Jingwen, et al., Preparation and characterization of new polyacrylamide hydrogels with ultrahigh mechanical strength and super elastic, Synthetic Technology & Application, 2019, pp. 13-19, vol. 34, No. 4.

*Primary Examiner* — Phillip A Gray
(74) *Attorney, Agent, or Firm* — Bayramoglu Law Offices LLC

(57) ABSTRACT

A preparation method of a colchicine (COL) hydrogel microneedle (MN) is provided, including the following steps: dissolving an acrylamide (AM), N,N'-bis(acryloyl) cysteamine (BACA), and Irgacure 2959 in ultrapure water to
(Continued)

obtain a clear gel solution; pouring the clear gel solution into a polydimethylsiloxane (PDMS) mold, conducting low-speed centrifugation, and conducting an ultrasonic treatment to eliminate air bubbles; irradiating the PDMS mold under ultraviolet light, and air-drying in an oven to obtain a hydrogel MN; and adding a COL solution to the hydrogel MN, allowing swelling, air-drying, and demolding. The present disclosure overcomes the shortcoming that cross-linking points are unevenly distributed in the ordinary hydrogel MNs. The hydrogel MN prepared by the present disclosure has a complete needle shape, a neat matrix arrangement, cross-linking points evenly distributed in a network, and excellent mechanical toughness and a superior swelling capacity.

6 Claims, 19 Drawing Sheets

(51) Int. Cl.
  *B29C 37/00* (2006.01)
  *B29C 41/04* (2006.01)
(52) U.S. Cl.
  CPC ..... *B29C 41/04* (2013.01); *A61M 2037/0053* (2013.01); *B29C 2035/0827* (2013.01)
(58) Field of Classification Search
  CPC ............ B29C 41/04; B29C 2035/0827; A61K 31/165; A61K 41/00
  USPC ......................................................... 604/173
  See application file for complete search history.

(56) References Cited

FOREIGN PATENT DOCUMENTS

| | | |
|---|---|---|
| CN | 114432275 A | 5/2022 |
| CN | 115337530 A | 11/2022 |

\* cited by examiner

COLCHICINE HYDROGEL MICRONEEDLE AND PREPARATION METHOD THEREOF

CROSS REFERENCE TO THE RELATED APPLICATIONS

This application is the national phase entry of International Application No. PCT/CN2023/081347, filed on Mar. 14, 2023, which is based upon and claims priority to Chinese Patent Application No. 202211077519.0, filed on Sep. 5, 2022, the entire contents of which are incorporated herein by reference.

TECHNICAL FIELD

The present disclosure relates to the technical field of medicine, and specifically to a colchicine (COL) hydrogel microneedle (MN) and a preparation method thereof.

BACKGROUND

Gout is common inflammatory arthritis in both developed and developing countries. Gout is triggered by the accumulation of monosodium urate (MSU) crystals. Acute gouty arthritis (AGA) is characterized by extreme pain, swelling, fever, and difficult motion of affected joints, which severely affect the daily life. Therefore, AGA has always been the focus of basic research in the entire medical field. Currently, there are several effective treatments to alleviate the pain and inflammatory response of AGA, for example, various inflammatory factors such as tumor necrosis factor (TNF)-$\alpha$, interleukin (IL)-6, and IL-1$\beta$ are inhibited to inhibit the function of inflammatory cells. Non-steroidal anti-inflammatory drugs (NSAIDs), corticosteroids, COL, or the like can be used to reduce the inflammatory response. However, the frequent oral administration of COL can lead to adverse reactions, such as side effects in the gastrointestinal tract. In 2007, the COL patch was registered as a drug, which may provide new opportunities in the field of transdermal administration. While the transdermal administration method can overcome the above limitations, the high water solubility and poor skin permeability of COL make the transdermal administration challenging.

MN is a novel painless transdermal administration technology with a promising application prospect and high safety. Hydrogel MNs have a high drug-loading capacity and adjustable drug release compared with other MNs, which avoids a toxic response caused by the burst release of COL. In general, hydrogel MNs have a specified hardness in a dry state, and can absorb an interstitial fluid and expand into a 3D network after entering the skin to release a drug. The above factors are often directly related to a cross-linking ratio of a polymer. However, the uneven distribution of cross-linking points in a network of a polymer makes the traditional hydrogel MNs have weak brittleness, making it difficult to use these hydrogel MNs in the skin with a thick stratum corneum at elbow joints. The incompatibility between mechanical properties and swelling properties of hydrogel MNs makes it difficult for the hydrogel MNs to release a drug within a reasonable application time.

Therefore, the development of a COL hydrogel MN with high swellability and high mechanical toughness has important prospects.

SUMMARY

In order to overcome the shortcomings and deficiencies of the prior art, a primary objective of the present disclosure is to provide a preparation method of a COL hydrogel MN. A COL hydrogel MN prepared by the preparation method has high swellability and high mechanical toughness.

The present disclosure is implemented by the following technical solutions:

The present disclosure provides a preparation method of a COL hydrogel MN, including the following steps:
(1) dissolving an acrylamide (AM), N,N'-bis(acryloyl) cysteamine (BACA), and Irgacure 2959 in ultrapure water to obtain a clear gel solution;
(2) pouring the clear gel solution into a polydimethylsiloxane (PDMS) mold, conducting low-speed centrifugation, and conducting an ultrasonic treatment to eliminate air bubbles;
(3) irradiating the PDMS mold with the clear gel solution under ultraviolet light, and air-drying in an oven to obtain a hydrogel MN; and
(4) adding a COL solution to the hydrogel MN, allowing swelling, air-drying, and demolding to obtain the COL hydrogel MN.

Preferably, in the step (1), mass proportions of the AM, the BACA, and the Irgacure 2959 in the clear gel solution are 10 wt % to 35 wt %, 0.01 wt % to 0.1 wt %, and 0.01 wt % to 0.2 wt %, respectively.

Preferably, in the step (2), the low-speed centrifugation is conducted at 3,000 rpm to 4,000 rpm for 5 min to 20 min.

Preferably, in the step (3), the irradiating under the ultraviolet light is conducted for 10 min to 60 min at 315 nm to 400 nm and 100 W to 500 W.

The present disclosure also provides a COL hydrogel MN prepared by the preparation method described above.

Compared with the prior art, the present disclosure has the following beneficial effects:
(1) The hydrogel MN of the present disclosure is prepared from a highly-hydrophilic monomer (AM) and a cross-linking agent (BACA) with an ultraviolet light-responsive disulfide bond. The present disclosure overcomes the shortcoming that cross-linking points are unevenly distributed in the ordinary hydrogel MNs. The hydrogel MN prepared by the present disclosure has a complete needle shape, a neat matrix arrangement, cross-linking points evenly distributed in a network, and excellent mechanical toughness (higher than 10 N/needle) and a superior swelling capacity (higher than 2500%).
(2) The COL hydrogel MN prepared by the present disclosure has a cumulative release rate of greater than 80% within 48 h, a release curve conforming to the first-order equation, and biocompatibility, and can effectively treat the inflammation of acute gout in rats. The present disclosure provides a new idea and strategy for the development and treatment of novel therapeutic dosage forms of COL.

BRIEF DESCRIPTION OF THE DRAWINGS

FIGS. 2A-2B show the influence of the monomer AM on a force-displacement curve and a swelling ratio of the MN (n=3), FIGS. 2C-2D show the influence of the photoinitiator (Irgacure 2959) on a force-displacement curve and a swelling ratio of the MN (n=3), and FIGS. 2E-2F show the influence of the cross-linking agent (BACA) on a force-displacement curve and a swelling ratio of the MN (n=3);

FIG. 3A is a picture of the MN; FIG. 3B is an optical microscopic image of the MN, 4×; FIG. 3C shows the comparison of the MN of the present disclosure under an optical microscope (lower, 4×) and a calcein MN under an inverted fluorescence microscope (upper, 5×); FIGS. 3D-3E show scanning electron microscopy (SEM) images of the MN; and FIG. 3F shows an SEM image of a lyophilized MN with a porous structure;

FIG. 6A shows force-displacement curves of MNs prepared from different cross-linking agents and initiators, where (i) is a force-displacement curve for MN prepared with BACA as a cross-linking agent and Irgacure 2959 as a photoinitiator, (ii) is a force-displacement curve for blank-MN prepared with N,N-methylenebis(acrylamide) (MBA) as a cross-linking agent and Irgacure 2959 as a photoinitiator, and (iii) is a force-displacement curve for blank-MN prepared with BACA as a cross-linking agent and $K_2O_8S_2$ as a photoinitiator; FIG. 6B shows a swelling rate-time curve of the MN of the present disclosure (n=3); FIG. 6C shows cumulative transdermal drug release and first-order kinetic fitted curves of the COL MN (n=6); and FIG. 6D shows images under a confocal microscope for a skin penetration behavior of the calcein MN released into the skin in vitro;

FIG. 7A shows an insertion rate of each Parafilm®, layer; FIG. 7B shows the methylene blue staining of insertion holes in the skin of a rat; and FIG. 7C shows an image of the calcein MN inserted into the skin under a confocal microscope;

FIG. 8A shows the influence of blank-MN, COL MN, and a COL solution on a survival rate of human immortalized epidermal cells (HaCaT); and FIG. 8B shows images of hematoxylin-eosin (H&E)-stained sections and terminal deoxynucleotidyl transferase (TdT) dUTP Nick-End Labeling (TUNEL)-stained sections obtained after the MN in each group is applied to the abdominal skin of rats;

FIG. 9A shows the comparison of images of edema of a left ankle joint injected with a MSU crystal suspension and a right ankle joint injected with saline; FIG. 9B shows changes of volumes of paws after rat ankle joints are injected with the MSU crystal suspension and the saline over time (n=6); FIG. 9C shows the swelling of toes of rats with acute gout after a COL-MN treatment; and FIGS. 9D-9F show serum inflammatory factors IL-1β (FIG. 9D), IL-6 (FIG. 9E), and TNF-α (FIG. 9F) levels in rats after the treatment, respectively.

DETAILED DESCRIPTION OF THE EMBODIMENTS

The present disclosure is further explained below through specific embodiments. The following examples are the preferred embodiments of the present disclosure, but the implementations of the present disclosure are not limited by the following examples.

Performance Test Methods:

1.1 Characterization by a Texture Analyzer

The standard mechanical testing was conducted for MN under a compression mode of the TMS-Pilot texture analyzer. A needle was taken from MN and placed on a stainless steel base plate of the texture analyzer with a tip facing up. A cylindrical probe with a diameter of 6 mm was allowed to fall at a speed of 30 mm/min, and when the cylindrical probe was in contact with a needle array, a trigger force of 0.03 N was applied and continuously kept until a displacement of 0.3 mm occurred.

1.2 Characterization of Swelling

A swelling capacity of MN was calculated according to the $(M_t-M_0)/M_0$ equation, where $M_0$ and $M_t$ represent masses of a hydrogel in each formula before and after being soaked in phosphate buffered saline (PBS, 7.4) for 0 h to 24 h, respectively.

1.3 CRITIC Weighting Analysis

Data was normalized with the SPSSAU software (https://spssau.com/) to eliminate unit dimensions, and the variability, conflict, information content, weighting coefficient, and comprehensive score of indicators were calculated.

Example 1

A preparation method of a COL hydrogel MN was provided, including the following steps:
(1) 1 g of AM, 2 mg of BACA, and 5 mg of Irgacure 2959 were dissolved in 5 mL of ultrapure water to obtain a clear gel solution.
(2) The clear gel solution was poured into a PDMS mold, and the PDMS mold was subjected to low-speed centrifugation (3,500 rpm, 5 min) and then to an ultrasonic treatment to eliminate air bubbles.
(3) The PDMS mold with the clear gel solution was irradiated under ultraviolet light (365 nm, 300 W) for 20 min, and then air-dried in an oven to obtain a hydrogel MN (blank-MN).
(4) A COL solution was added to the hydrogel MN, swelling was allowed for 12 h, and then air-drying and demolding were conducted to obtain the COL hydrogel MN (COL-MN).

Comparative Example 1

This comparative example was different from Example 1 in that, in the step (1), MBA was adopted as a cross-linking agent instead of the BACA.

Comparative Example 2

This comparative example was different from Example 1 in that, in the step (1), 30 mg of potassium persulfate ($K_2O_2S_2$) was adopted as an initiator instead of Irgacure-2959, and in the step (3), the heating in an oven for 6 h was adopted instead of the irradiating under ultraviolet light for 20 min.

Figure 6A:
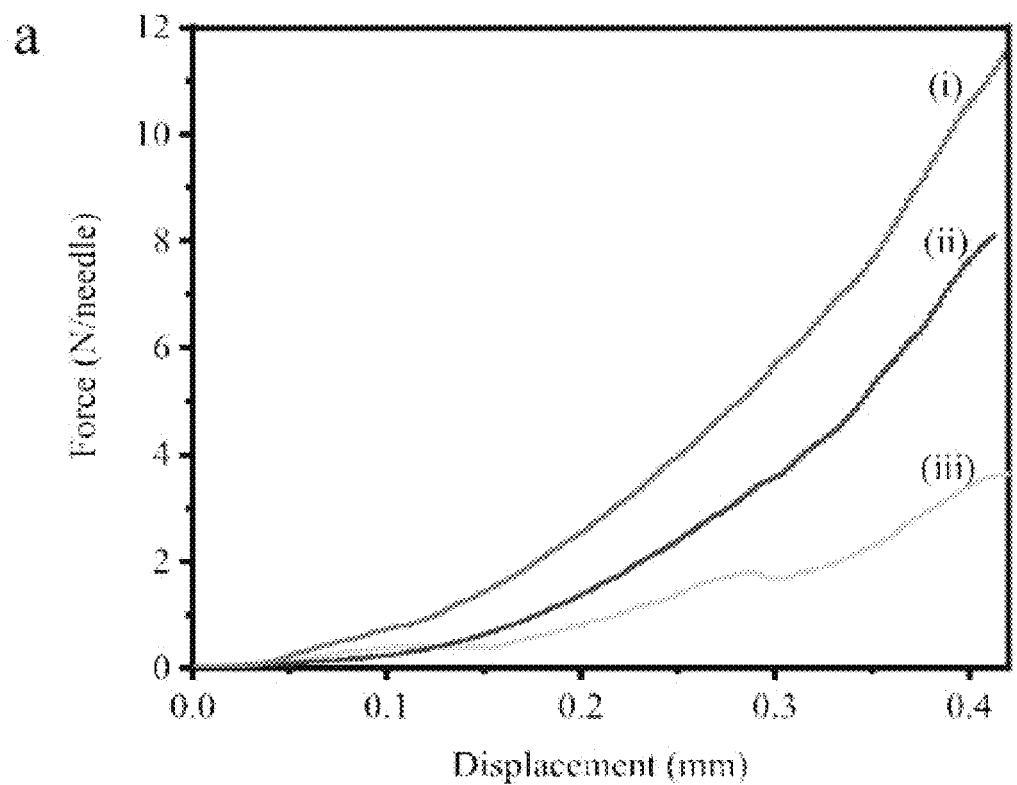
FIGS. 6A-6D show the in vitro characterization of the MN of the present disclosure, where

The MNs prepared in Example 1 and Comparative Examples 1 to 2 each were subjected to standard mechanical testing under a compression mode of the TMS-Pilot texture analyzer, and results were shown in FIG. 6A. A rupture force of the MN in Example 1 is 11.53 N/needle, a rupture force of the MN in Comparative Example 1 is 8.11 N/needle, and a rupture force of the MN in Comparative Example 2 is 3.61

N/needle. Example 1 requires a larger rupture force than Comparative Examples 1 and 2 to allow a same amount of compression, indicating that Example 1 has a higher mechanical strength than Comparative Examples 1 and 2. Previous studies have proved that each needle requires a force of greater than 0.058 N to be inserted into the skin. A displacement of the MN in Example 1 under a required force is less than 0.1 mm, indicating that the MN prepared by the present disclosure has a sufficient mechanical strength to penetrate the skin.

Figure 1:
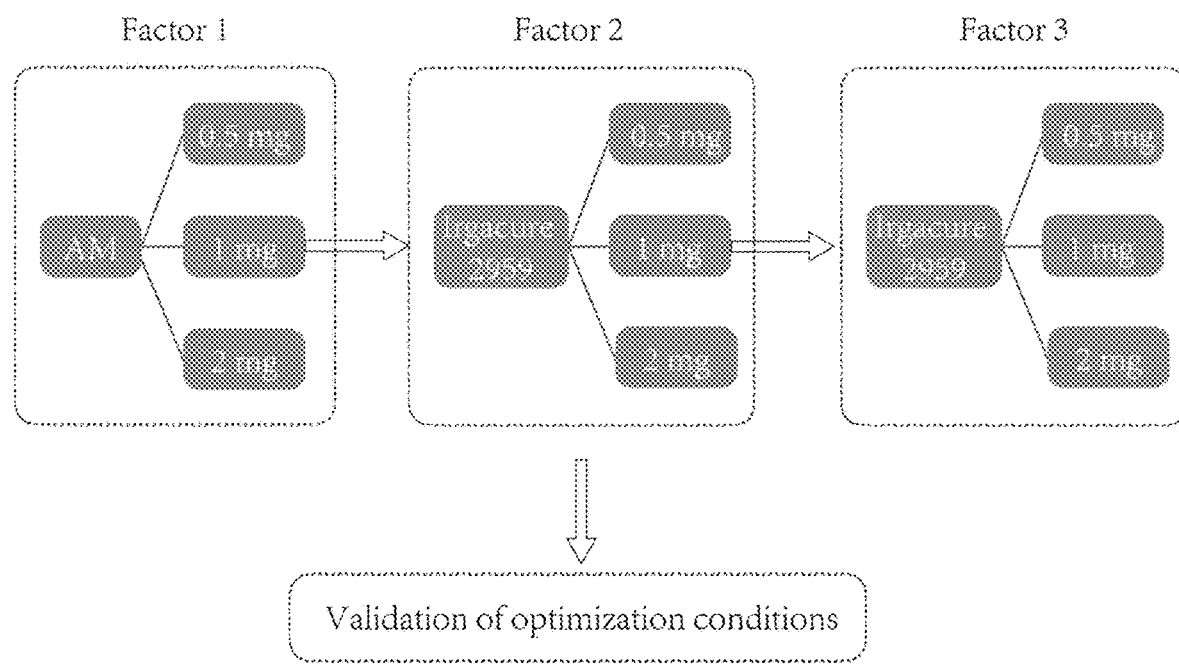
FIG. 1 is a schematic diagram of continuous single-factor optimization.

In addition, the present disclosure has found through research that the contents of the AM monomer, the cross-linking agent (BACA), and the photoinitiator have relatively-large impacts on the physical and chemical properties of hydrogel MN. Therefore, in the present disclosure, the process parameters for MN were optimized through continuous single-factor experiments, and the influence of gel solutions produced by adding AM (0.5 g, 1 g, and 2 g), Irgacure 2959 (1 mg, 5 mg, and 10 mg), and BACA (1 mg, 2 mg, and 4 mg) at different contents to 5 mL of pure water on a rupture force of Blank-MN and swelling of a hydrogel was investigated. The factor levels were shown in Table 1 below, and the comparison was conducted in the order according to FIG. 1:

TABLE 1

| Formulation | AM (g) | Irgacure 2959 (mg) | BACA (mg) |
|---|---|---|---|
| AM 0.5 g | 0.5 | 1 | 1 |
| AM 1 g | 1 | 1 | 1 |
| AM 2 g | 2 | 1 | 1 |
| Irgacure-2959 1 mg | 1 | 1 | 1 |
| Irgacure-2959 5 mg | 1 | 5 | 1 |
| Irgacure-2959 10 mg | 1 | 10 | 1 |
| BACA 1 mg | 1 | 5 | 1 |
| BACA 2 mg | 1 | 5 | 2 |
| BACA 4 mg | 1 | 5 | 4 |

Figure 2A:
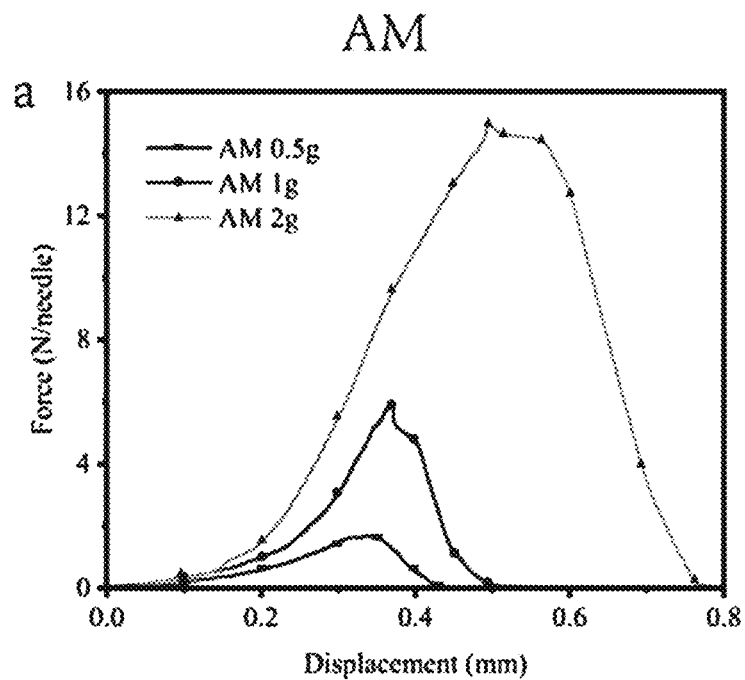
FIGS. 2A-2F show results of a study on the influence of gel solutions produced by adding AM (0.5 g, 1 g, and 2 g), Irgacure 2959 (1 mg, 5 mg, and 10 mg), and BACA (1 mg, 2 mg, and 4 mg) at different contents to 5 mL of water on a rupture force of the hydrogel MN of the present disclosure and a swelling behavior of a hydrogel in the hydrogel MN of the present disclosure, where
Figure 2B:
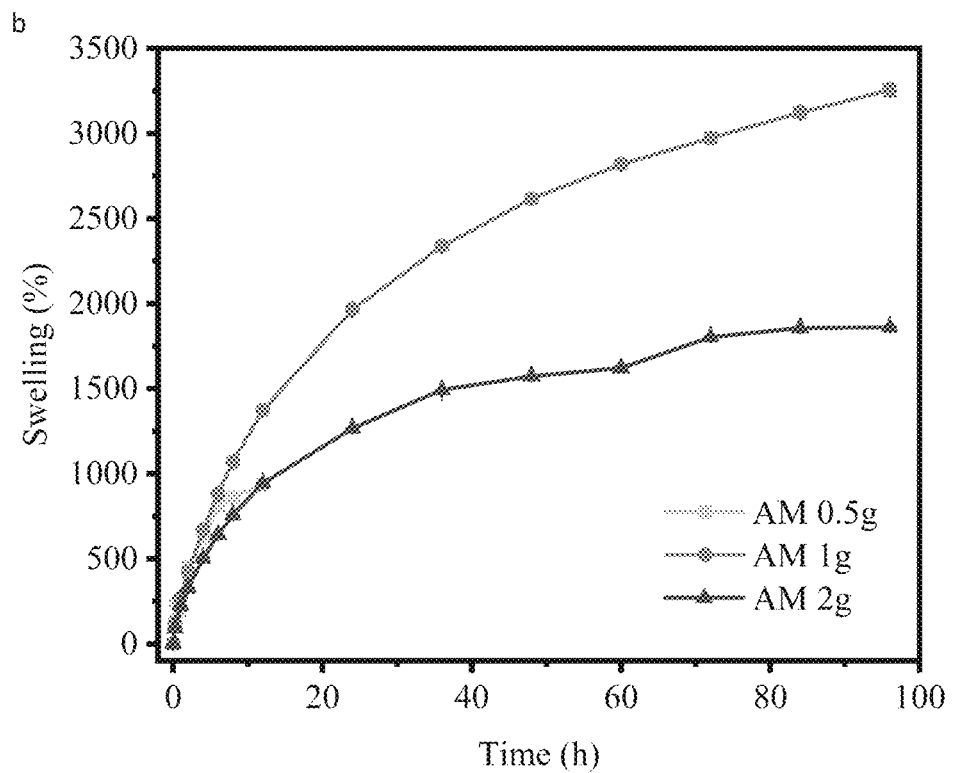
Figure 2C:
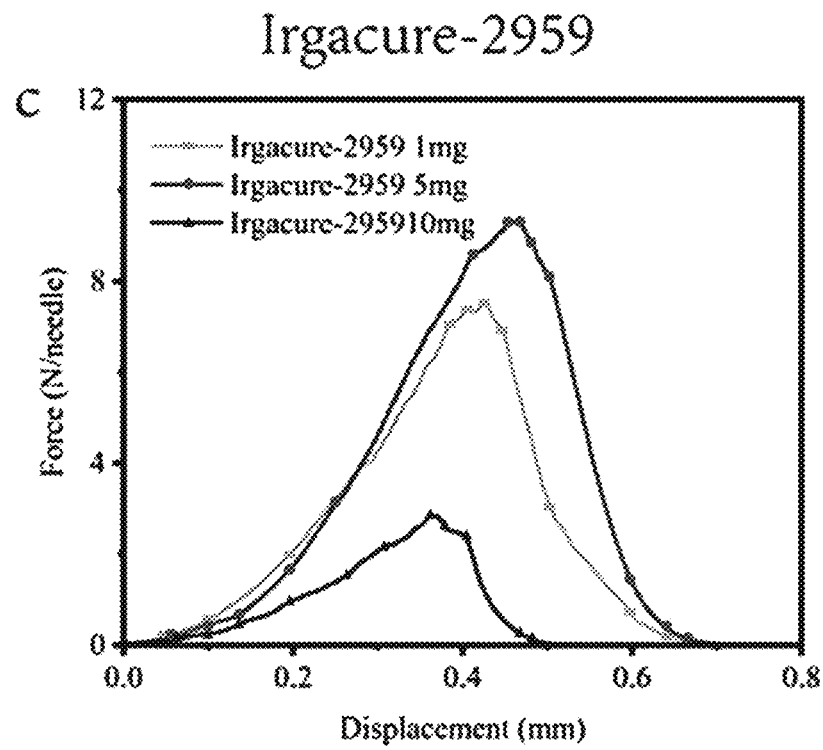
Figure 2D:
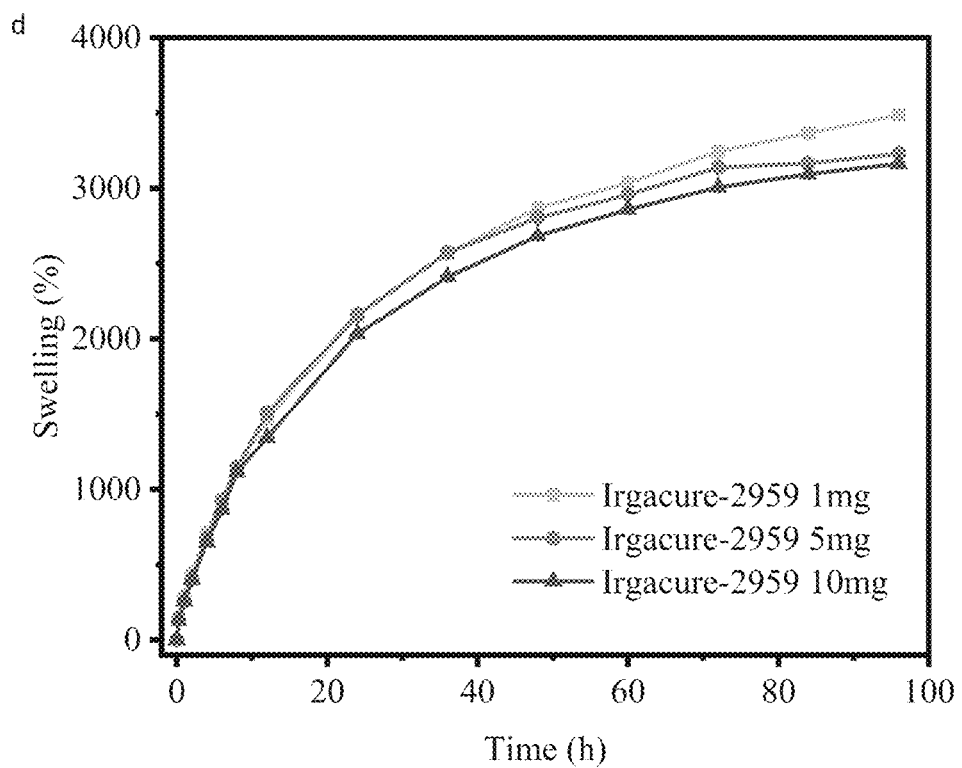
Figure 2E:
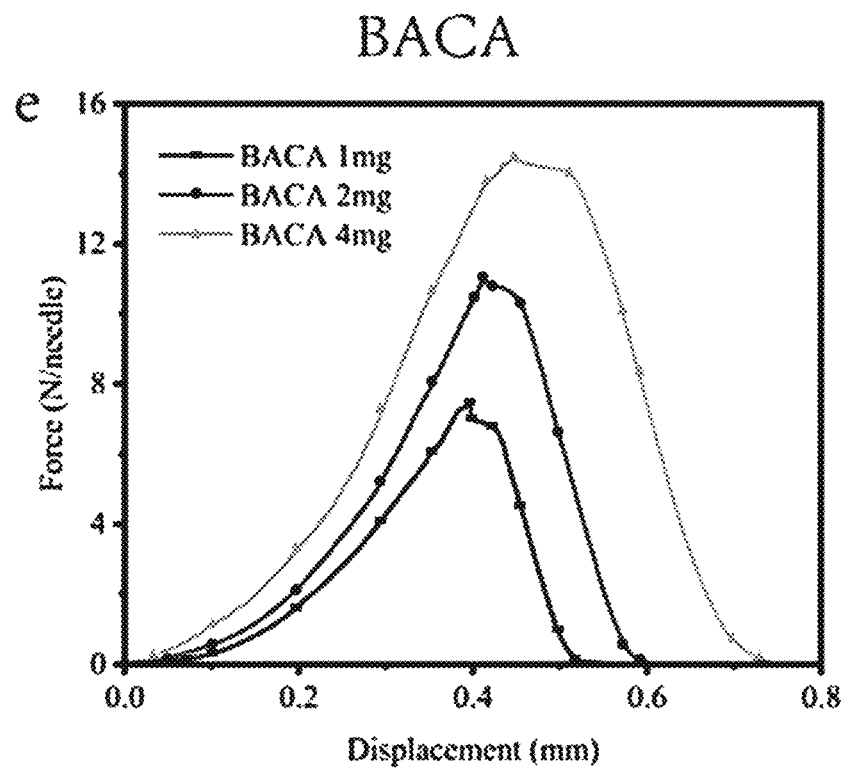
Figure 2F:
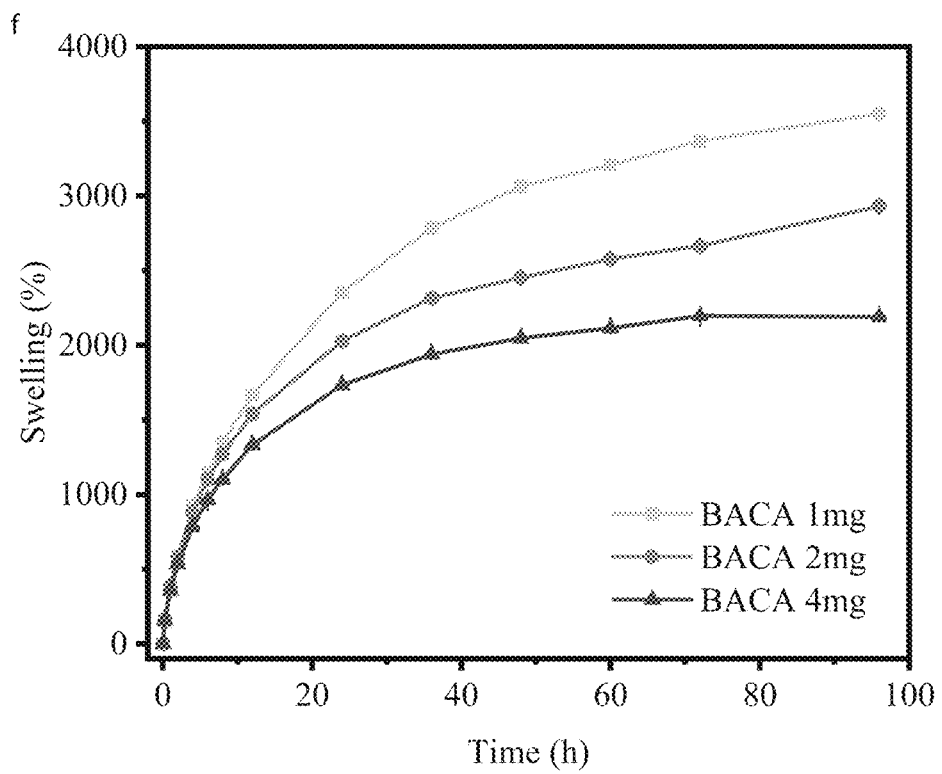

As shown in FIGS. 2A-2F and Tables 2 and 3, when a content of AM in an MN solution is 0.5 g, the mechanical fracture occurs and the structural integrity of a hydrogel network losses because the swelling exceeds an intrinsic elastic strength (FIG. 2B). In addition to this condition, weighting coefficients of the two indicators of a rupture force and a swelling degree were weighted by the CRITIC weighting method to obtain a comprehensive score integrating the above two properties. The variability, conflict, information content, and weighting coefficient of the rupture force are almost equal to those of the swelling degree (Table 2), indicating that the two indicators have low reproducibility and high conflict.

The indicators and comprehensive score in each group are shown in Table 3. The comprehensive score results show that MN of the "AM 1 mg" formula is as important as MN of the "AM 2 mg" formula. Therefore, the MN "AM 1 mg" with a high swelling degree is selected for subsequent screening. A concentration of Irgacure2959 does not have a significant impact on a swelling degree of a hydrogel (FIG. 2D), and a weight of the rupture force is high (Table 2). According to the comprehensive scores, the "Irgacure-2959 5 mg" MN with a large rupture force is selected (Table 3). Similarly, the "BACA 2 mg" MN with a high comprehensive score is finally selected as the optimal formula (Table 3).

TABLE 2

| Factor | Item | Variability | Conflict | Information content | weight |
|---|---|---|---|---|---|
| AM | MMS_Rupture force (N) | 0.707 | 2 | 1.414 | 50% |
|  | MMS_Swelling (%) | 0.707 | 2 | 1.414 | 50% |
| Irgacure 2959 | MMS_Rupture force (N) | 0.564 | 1.281 | 0.722 | 51.62% |
|  | MMS_Swelling (%) | 0.528 | 1.281 | 0.677 | 48.38% |
| BACA | MMS_Rupture force (N) | 0.5 | 1.999 | 0.999 | 49.97% |
|  | MMS_Swelling (%) | 0.501 | 1.999 | 1.001 | 50.03% |

TABLE 3

| Factor | Lever | Rupture force (N) | Swelling (%) | comprehensive score |
|---|---|---|---|---|
| AM | 1 g | 6.22 | 3255.36 | 0.50 |
|  | 2 g | 15.24 | 1860.72 | 0.50 |
| Irgacure 2959 | 1 mg | 3.48 | 3485.79 | 0.51 |
|  | 5 mg | 9.90 | 3228.78 | 0.62 |
|  | 10 mg | 3.15 | 3162.72 | 0.00 |
| BACA | 1 mg | 7.70 | 3549.46 | 0.50 |
|  | 2 mg | 11.21 | 2930.02 | 0.52 |
|  | 4 mg | 14.69 | 2190.34 | 0.50 |

Example 2 Apparent Characterization 2.1 Apparent Characterization of Hydrogel MNs A 3D structure of MN and a surface morphology of lyophilized MN were observed by optical microscopy and SEM. A fluorescence distribution of a tip of calcein MN was observed under an inverted fluorescence microscope. The elements C, H, O, and S of a tip of MN were scanned by EDS.

Hydrogel MN was a product (blank-MN) obtained by the steps (1) to (3) in Example 1. Lyophilized MN was prepared by the steps (1) to (3) in Example 1 except that lyophilizing was adopted instead of the air-drying in the step (3). Calcein MN was prepared by the steps (1) to (4) in Example 1 except that calcein was adopted instead of COL in the step (1).

Figure 3A:
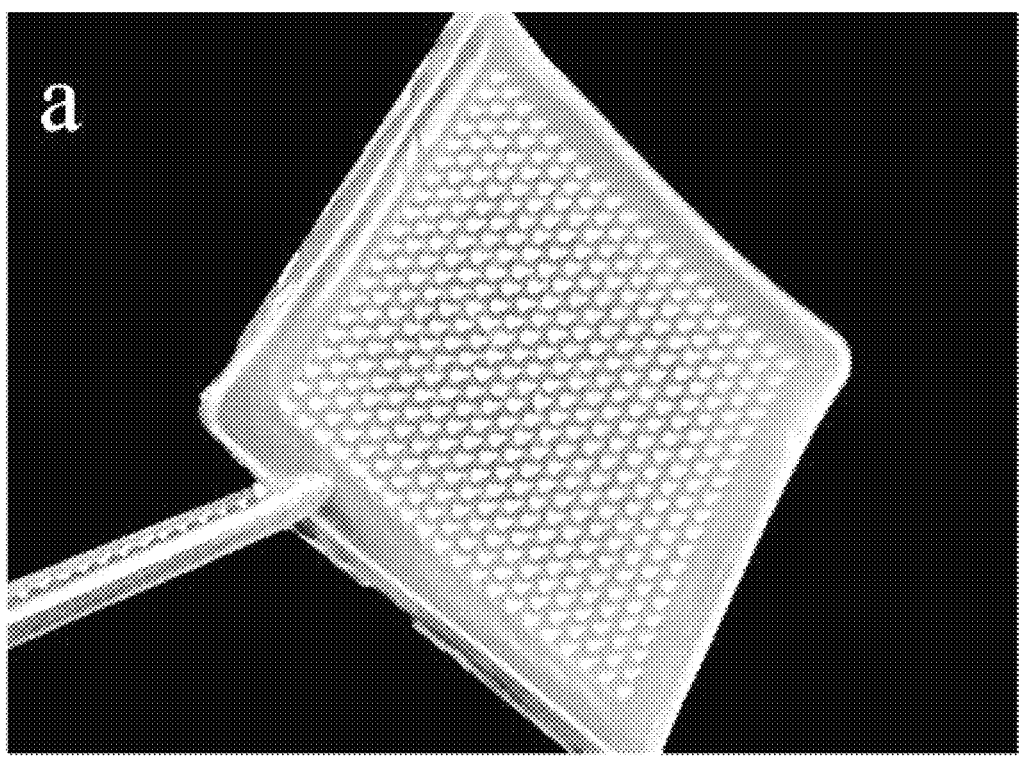
FIGS. 3A-3F show the apparent characterization of the MN of the present disclosure, where
Figure 3B:
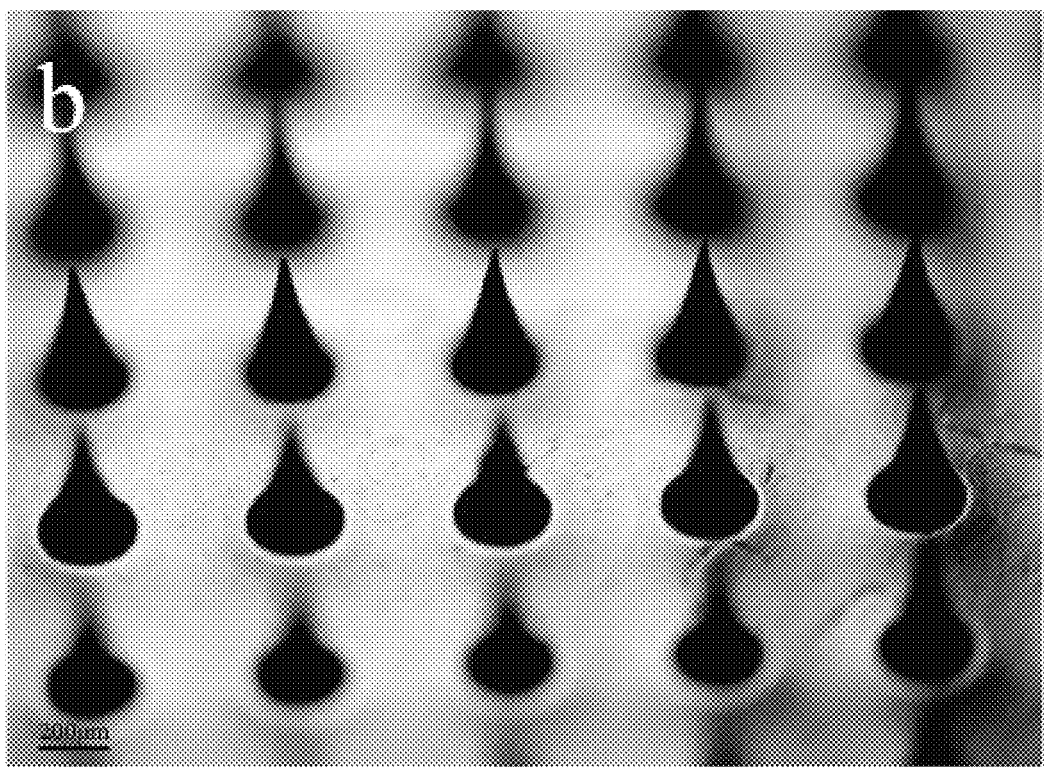
Figure 3C:
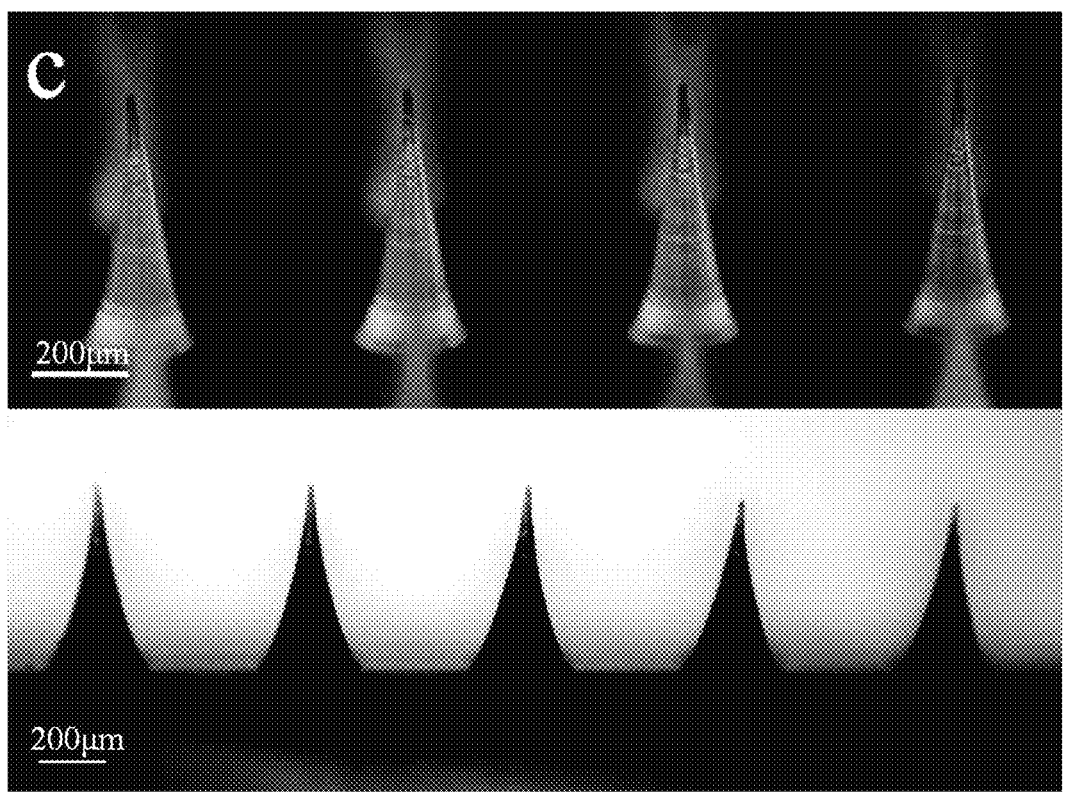
Figure 3D:
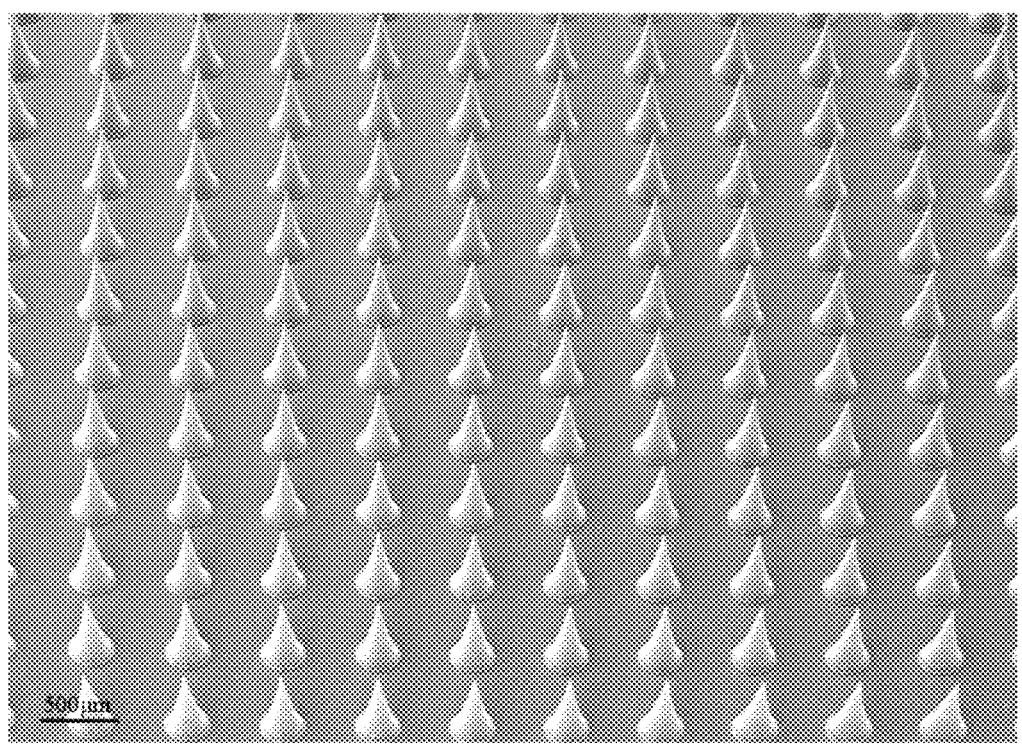
Figure 3E:
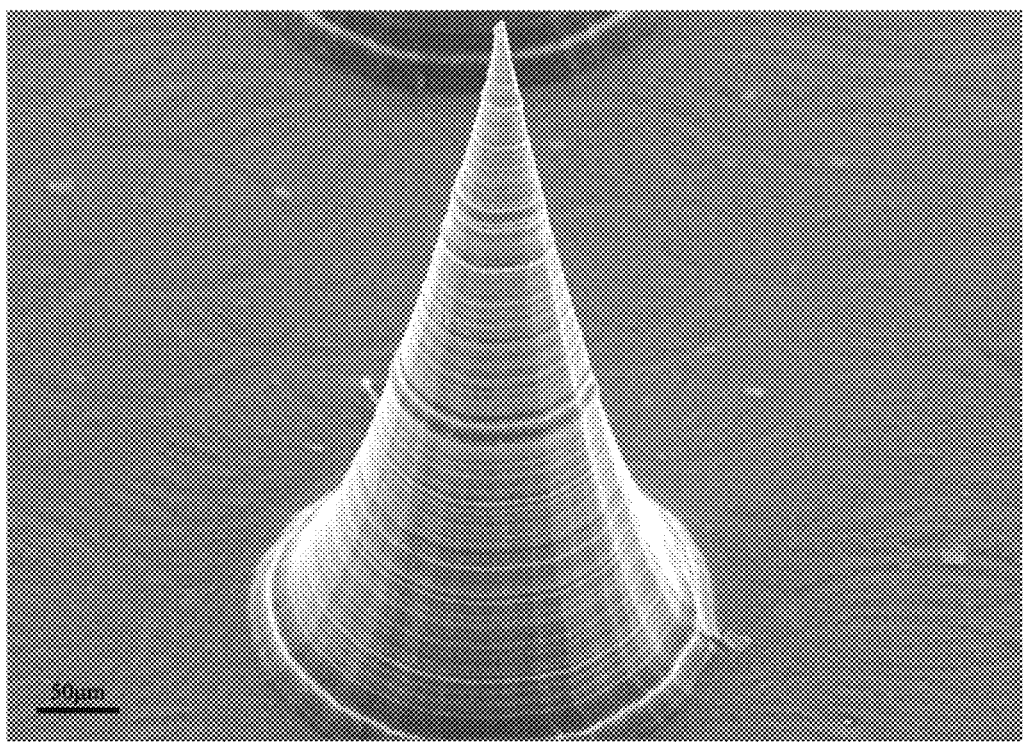
Figure 3F:
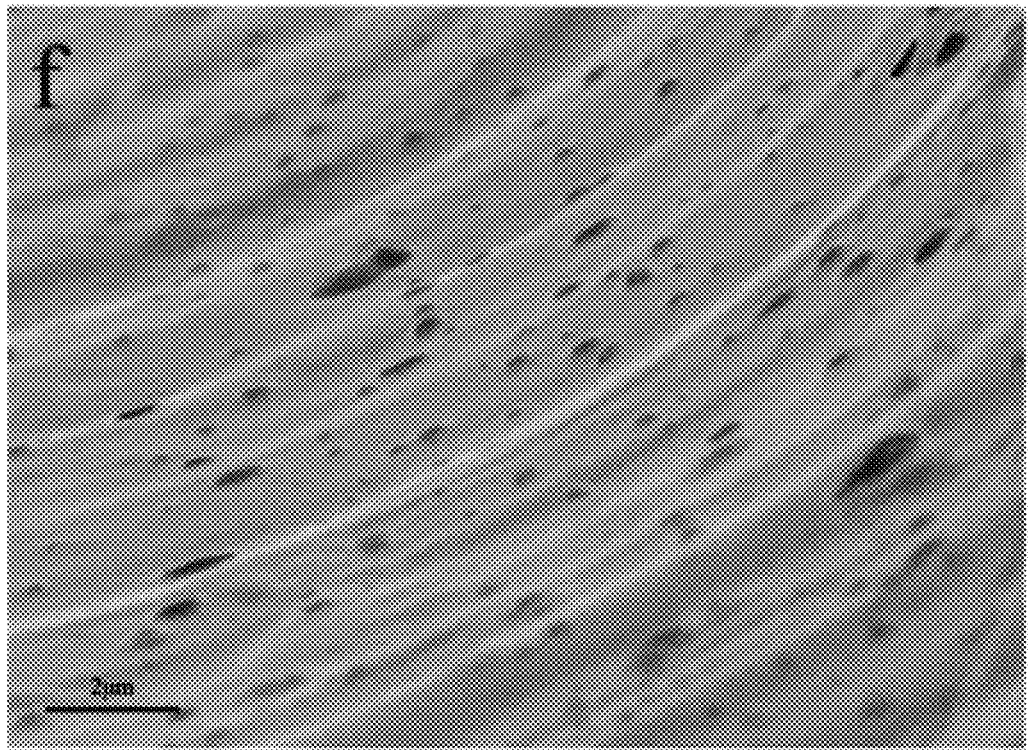
Figure 4:
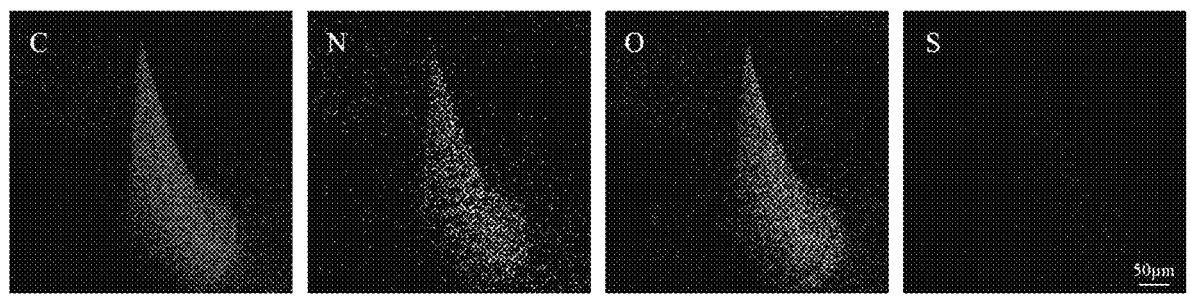
FIG. 4 shows energy-dispersive X-ray spectroscopy (EDS) images of the MN of the present disclosure.

With reference to FIGS. 3A-3F to FIG. 4, an array of 400 MNs arranged evenly was prepared (FIG. 3A). The optical microscopy shows a size of a sample with a height of about 500 µm and a bottom width of about 300 µm (FIG. 3B). Calcein is evenly distributed in a tip of the MN, indicating that the hydrophilic small-molecule compound can be uniformly distributed in the MN through swelling and de-swelling (FIG. 3C). The SEM shows that the MN has a regularly-conical shape, a sharp tip, and a multilayered structure similar to the human skin on a surface (FIGS. 3D-3E), which may be attributed to the fact that homopolymeric AM is not prone to protonation and a local potential energy will not be produced. The uniformity of a potential may be the reason for the uniformity of mechanical properties, and may also be the basic reason for determining macroscopically mechanical behaviors. The surface has uniform pores (FIG. 3F), and this porous structure facilitates the dissolution and diffusion of a drug. EDS results show that disulfide bonds are evenly distributed in the hydrogel MN (FIG. 4).

2.2 Apparent Characterization of COL Hydrogel MN

An apparent morphology of COL MN was observed under an optical microscope.

COL hydrogel MN was a product (COL-MN) obtained by the steps (1) to (4) in Example 1.

Figure 5:
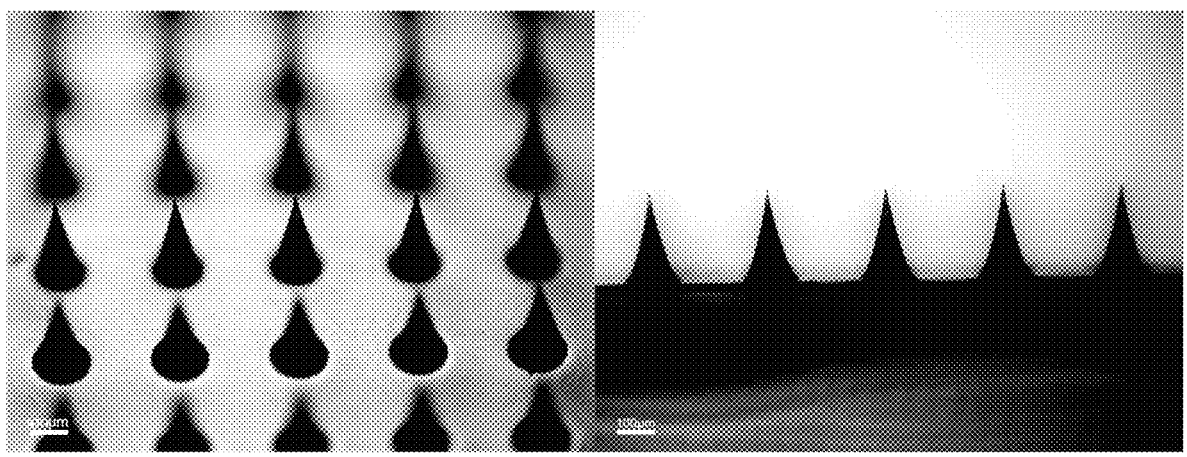
FIG. 5 shows microscopy images of the COL MN of the present disclosure.

As shown in FIG. 5, the COL hydrogel MN prepared in Example 1 has a prominent apparent structure, a sharp needle tip, a uniform array arrangement, and a uniform needle tip structure, and does not undergo a structural damage compared with the hydrogel MN.

Example 3 In Vitro Characterization of Hydrogel MNs 3.1 Characterization of a Swelling Degree of MN The MN in Example 1 was weighed by a balance with an initial weight m0. The MN was then soaked in 50 mL of PBS with pH 7.4 to allow swelling at room temperature for 24 h, then taken out, wiped with a filter paper to remove the excess surface water, and weighed, and a final weight was recorded as $m_t$. The swelling degree was calculated by the $(M_t-M_0)/M_0$ equation. Since PBS closely resembles the cutaneous interstitial fluid, PBS is selected as a swelling medium and used to simulate the cutaneous interstitial fluid in other similar studies.

Hydrogel MN was a product (blank-MN) obtained by the steps (1) to (3) in Example 1.

Figure 6B:
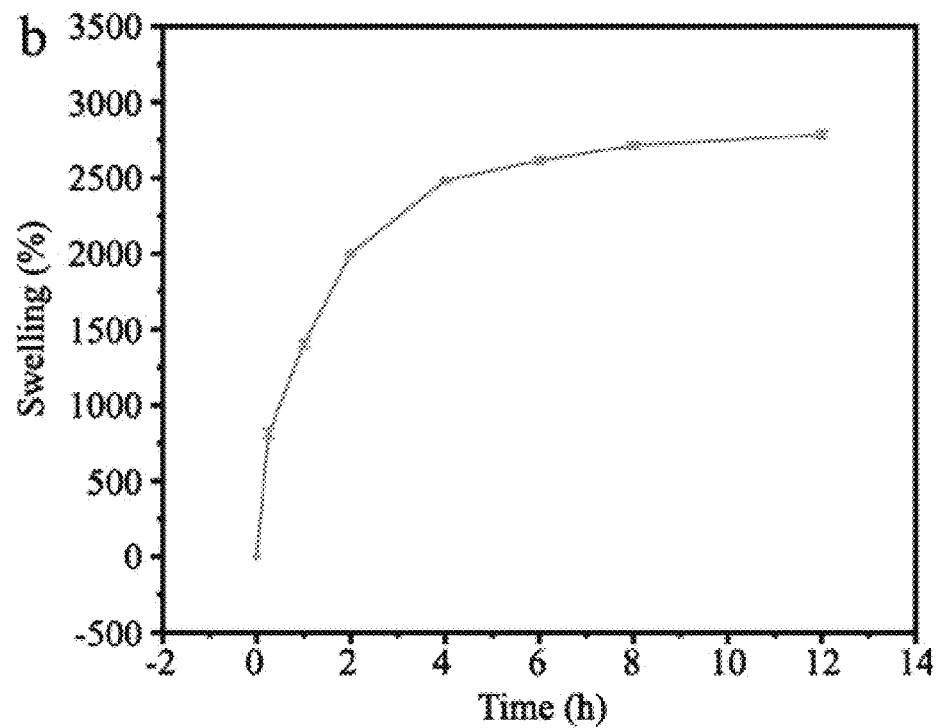

As shown in FIG. 6B, a swelling rate of the hydrogel MN (blank-MN) prepared by the present disclosure reaches equilibrium at 8 h, and a maximum swelling degree is 2708%.

3.2 In Vitro Transdermal Diffusion Experiment

The in vitro abdominal skin of a rat was taken from a −20° C. freezer, thawed, equilibrated in saline for 30 min, and then cut appropriately according to a diameter of a diffusion chamber. With a dermis layer at a bottom and an epidermis layer at a top, the abdominal skin was allowed to cover a plastic wrap. The epidermis layer was dried with a filter paper. The MN was applied for 30 s. A stirrer was added to a receiving unit. In the receiving unit, a rotational speed of the stirrer was 600 rpm and a temperature of the receiving unit was (32±0.2° C.). A stirrer and 10 mL of PBS (pH 7.4) were added to the diffusion chamber, and the diffusion chamber was kept at a constant temperature of 32° C. In the diffusion chamber, continuous stirring was conducted with the magnetic stirrer at a rotational speed of 600 rpm. A receptor cavity was filled with the PBS until the PBS was in contact with the skin, and then a timer was started.

At 1 h, 2 h, 4 h, 6 h, 8 h, 10 h, 12 h, 24 h, 36 h, and 48 h, 1 mL of a sample was automatically collected, and 1 mL of the PBS was automatically filled. A COL concentration in a sample was quantitatively analyzed through high-performance liquid chromatography (HPLC) (Waters Corporation, USA) with a Unitaryl C18 (4.6 mm×250 mm, 5 μm) chromatographic column, a mobile phase of methanol-water (60:40), a column temperature of 30° C., a detection wavelength of 254 nm, an injection volume of 10 μL, and a flow rate of 1.0 mL/min. A concentration of COL was calculated.

COL hydrogel MN was a product (COL-MN) obtained by the steps (1) to (4) in Example 1.

Figure 6C:
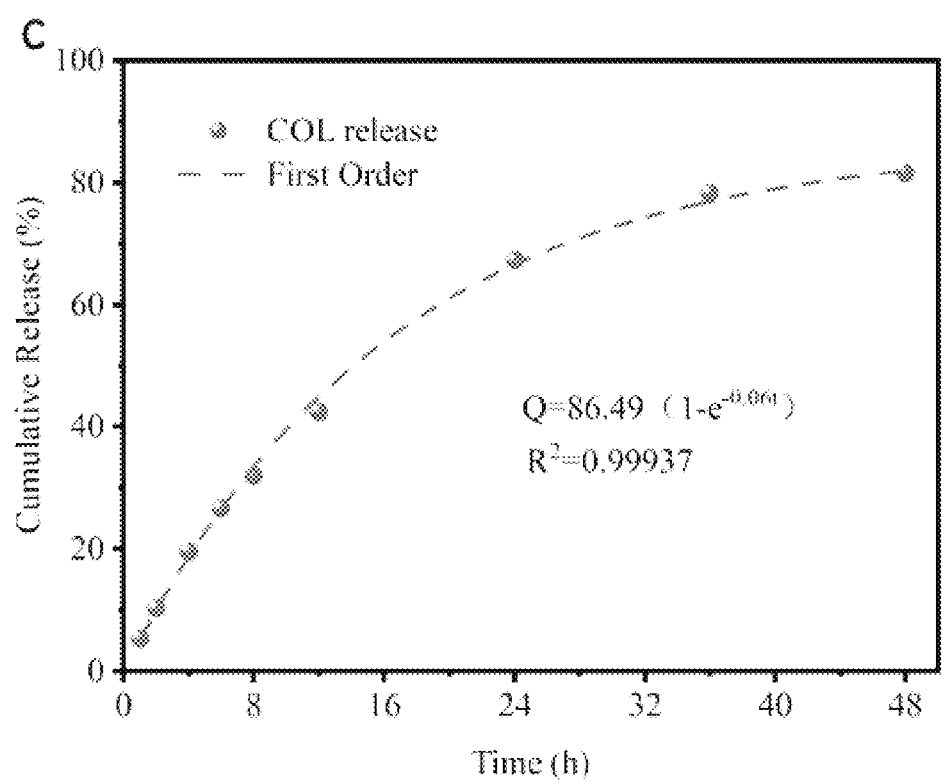

As shown in FIG. 6C, a cumulative release rate of the COL hydrogel MN (COL-MN) within 48 h can reach 80% or more, and a release curve is fitted by a first-order kinetic equation, indicating that the COL hydrogel MN (COL-MN) has a sustained release effect.

3.3 Study on an In Vitro Transdermal Diffusion Behavior of Drug-Loaded MN

The method was the same as in Example 1 except that calcein was adopted as a model drug instead of COL, and a diffusion behavior of the drug was characterized by a fluorescence distribution of calcein in the skin.

Calcein MN, the Bama miniature pig skin, and an automatic transdermal diffuser were adopted. The in vitro abdominal skin of a rat was taken from a −20° C. freezer, thawed, equilibrated in saline for 30 min, and then cut appropriately according to a diameter of a diffusion chamber. With a dermis layer at a bottom and an epidermis layer at a top, the abdominal skin was allowed to cover a plastic wrap. The epidermis layer was dried with a filter paper. The MN was applied for 30 s. A stirrer was added to a receiving unit. In the receiving unit, a rotational speed of the stirrer was 600 rpm and a temperature of the receiving unit was (32±0.2° C.). A stirrer and 10 mL of PBS (pH 7.4) were added to the diffusion chamber, and the diffusion chamber was kept at a constant temperature of 32° C. In the diffusion chamber, continuous stirring was conducted with the magnetic stirrer at a rotational speed of 600 rpm. A receptor cavity was filled with the PBS until the PBS was in contact with the skin, and then a timer was started. At 2 h, 6 h, 12 h, 24 h, and 48 h, a skin sample was collected, washed, frozen-sectioned, and observed under a laser scanning confocal microscope.

Figure 6D:
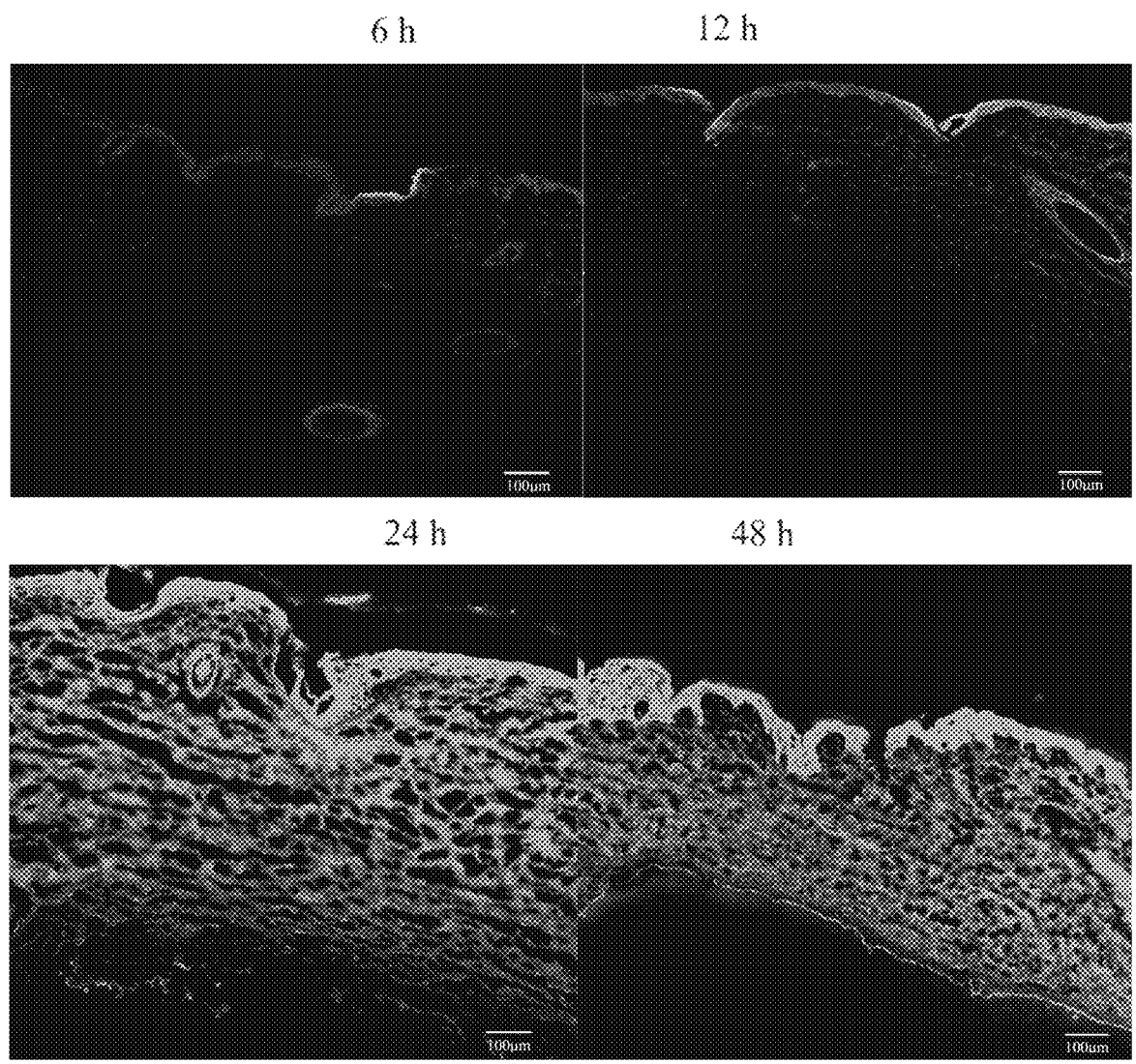

As shown in FIG. 6D, a process of drug penetration included a penetration process of a drug from MN to the skin and a diffusion process of the drug from the epidermis to the dermis. According to the fluorescence distribution, the former process was dominant within 12 h, the latter process was dominant from 12 h to 24 h, and calcein was still continuously released in the skin from 24 h to 48 h.

3.4 Study on the Insertion in Parafilm®

COL hydrogel MN was a product (COL-MN) obtained by the steps (1) to (4) in Example 1. Eight Parafilm® layers were arranged layer by layer with a depth of about 1 mm. The Parafilm® layers were placed on a piece of dental wax as a mechanical support, and a "thumb pressure" was applied to each array prototype of the COL hydrogel MN in Example 1. The penetration of the MN was assessed by counting a number of holes generated in each layer under an optical microscope. According to an equation (3), a percentage of holes in each layer was calculated.

Figure 7A:
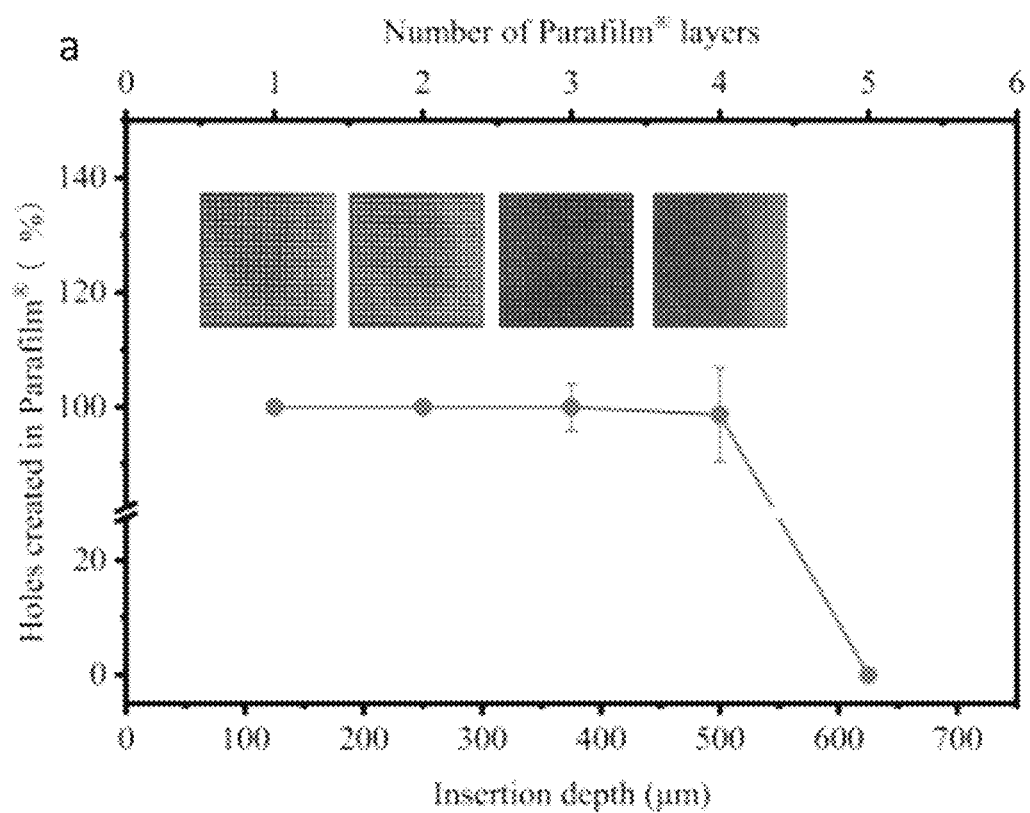
FIGS. 7A-7C show results of a study on the insertion of the MN of the present disclosure, where

FIG. 7A shows the penetration results of the COL hydrogel MN (COL-MN). An insertion rate of the COL hydrogel MN (COL-MN) is close to 100%, indicating that the COL hydrogel MN (COL-MN) prepared by the present disclosure has an sufficient ability to penetrate the skin.

3.5 Study on the Insertion in the In Vitro Abdominal Skin of a Rat

COL hydrogel MN was a product (COL-MN) obtained by the steps (1) to (4) in Example 1.

The abdominal skin of the rat was collected, subjected to subcutaneous adhesion removal, washed with saline, dried with a filter paper, wrapped with a plastic wrap, and stored in a 20° C. refrigerator. The MN was manually inserted into the rat skin for 10 min and then taken out. Then, a 1% methylene blue solution (100 L) was evenly distributed in holes for 10 min. The excess solution was absorbed with a filter paper, the skin was soaked in saline for washing, subjected to surface drying with a filter paper, and imaged.

Figure 7B:
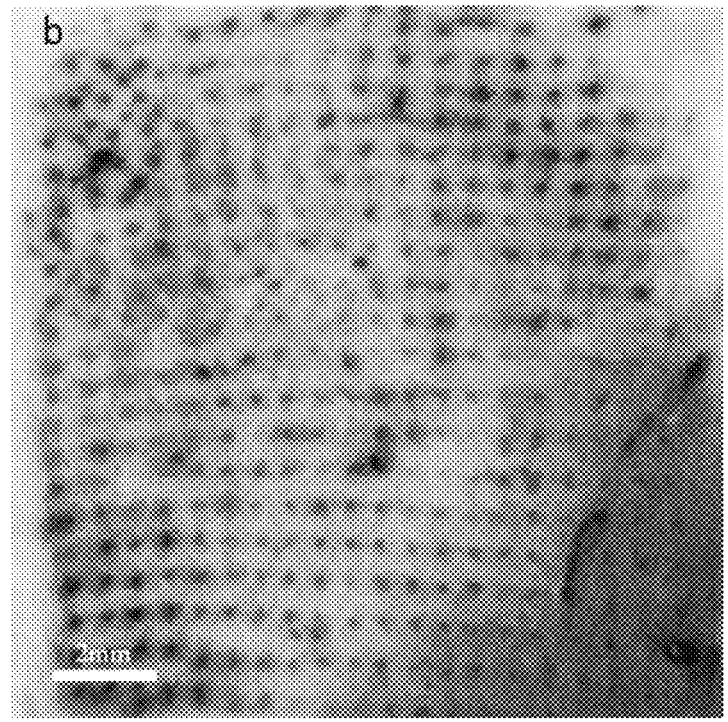

FIG. 7B shows that the COL hydrogel MN (COL-MN) prepared by the present disclosure can penetrate the skin with an efficiency close to 100%.

3.6 Study on the Insertion in the Pig Skin

Calcein was adopted as a model drug instead of COL.

Figure 7C:
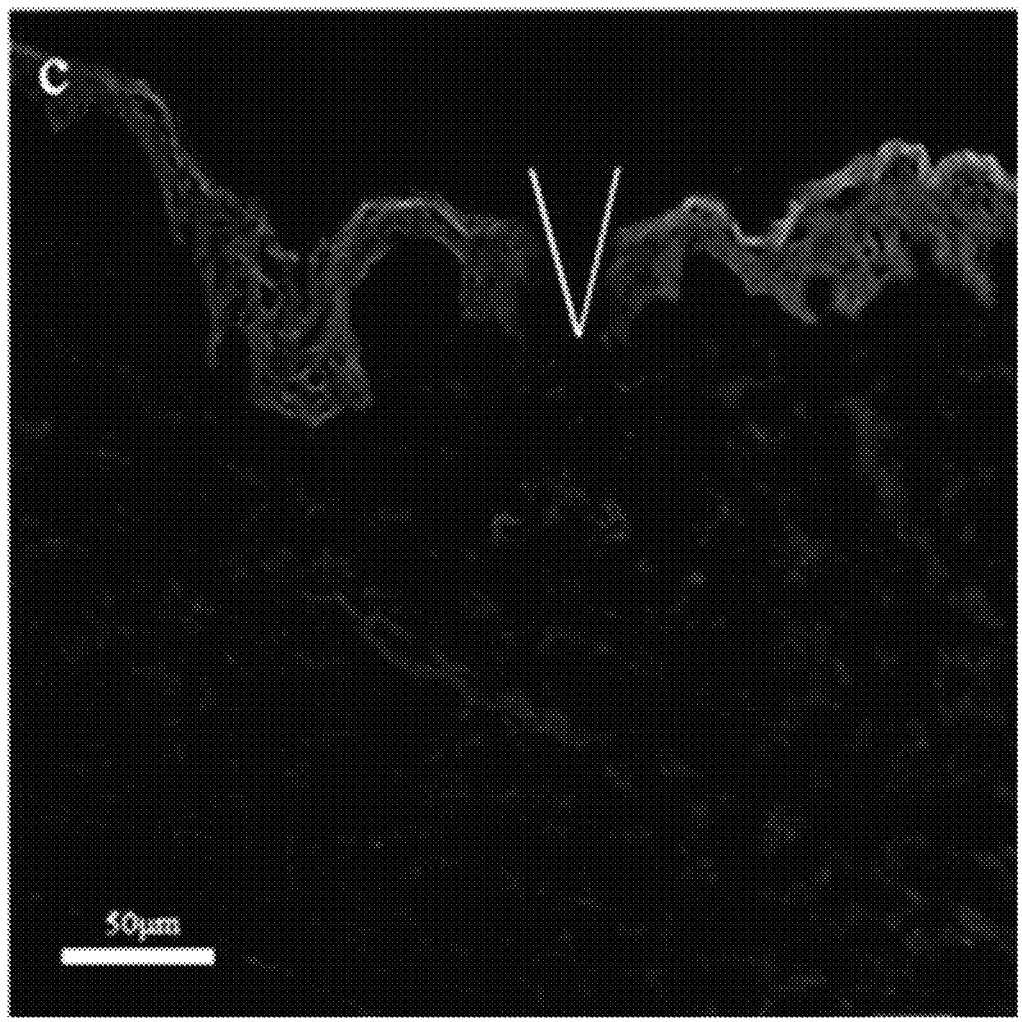

Immediately after calcein MN was applied to the pig skin for 48 h, the pig skin was cut into m-thick thin sections by a low-temperature ultramicrotome and observed under a laser scanning confocal microscope. FIG. 7C shows that the MN effectively penetrates the pig skin to form a microchannel.

Example 4 Study on In Vitro and In Vivo Biocompatibility of MNs 4.1 Cytotoxicity Study Blank-MN was a product obtained by the steps (1) to (3) in Example 1. COL-MN was a product obtained by the steps (1) to (4) in Example 1.

The cytotoxicity of each of 5 mg of COL and blank-MN and COL-MN (each including 5 mg of COL) for human keratinocytes (HaCaT) was detected with the CCK-8 kit. Before the study, 3 samples each were soaked in 10 mL of a DMEM complete medium for 24 h. HaCaT cells were inoculated in a 96-well plate at a density of $1\times10^6$ cells/well and cultivated overnight. The cells were then incubated in different sample-soaked solutions for 24 h. The treated cells were incubated with 10% CCK-8 for 1 h at 37° C., and the absorbance was measured at 450 nm with a microplate reader. The measurement was conducted three times. Results were expressed as cell viability percentages. Results of treated cells were compared with results of untreated control cells.

Figure 8A:
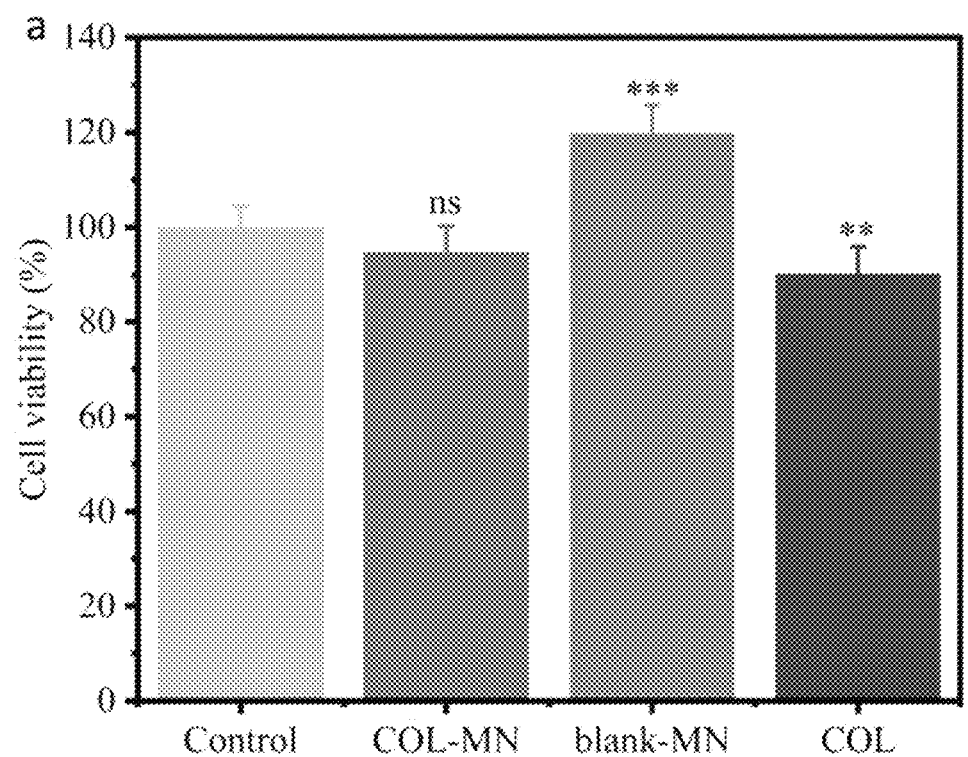
FIGS. 8A-8B show results of a study on the in vitro and in vivo biocompatibility of the MN of the present disclosure, where

As shown in FIG. 8A, blank-MN and COL-MN exhibit higher cell safety than the COL group.

4.2 Histopathology and Skin Tissue Cell Apoptosis Experiments

Blank-MN was a product obtained by the steps (1) to (3) in Example 1. COL-MN was a product obtained by the steps (1) to (4) in Example 1.

The abdominal skin of a rat was shaved. Then, blank-MN was applied for 24 h or 48 h and COL-MN was applied for 24 h or 48 h, where the fixation was conducted with a medical adhesive tape. At 24 h and 48 h, an abdominal skin tissue was collected, fixed with 10% neutral formalin for 18 h, embedded with paraffin, prepared into 4 m-thick sections, and stained with H&E and TUNEL to observe histopathological changes and apoptosis conditions, respectively. Inflammatory cells could be observed under a microscope, and apoptotic cells could be observed under a laser scanning confocal microscope.

Figure 8B:
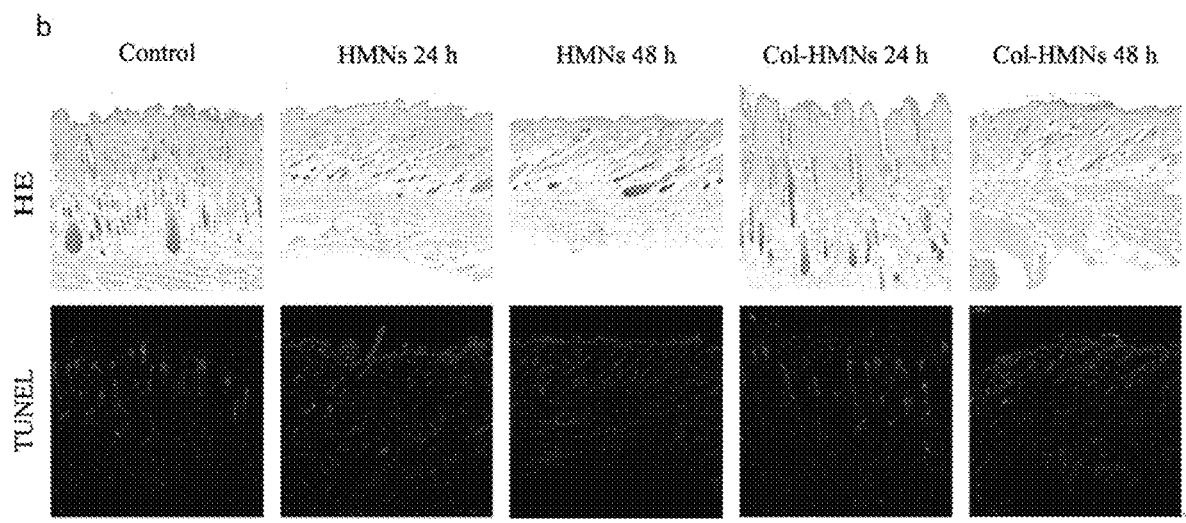

As shown in FIG. 8B, pathological changes of H&E-stained sections of the rat abdominal skin tissues treated with blank-MN and COL MN for 24 h and 48 h were observed under a microscope, and compared with pathological changes of a blank control group (untreated skin) to investigate the use safety of MNs. The blank-MN-treated skin sections exhibited almost similar cell integrity to the skin of the blank control group. The COL-MN-treated skin sections had no inflammation. However, due to a binding effect of COL to microtubules, COL-MN inhibited the cell proliferation to some extent, and exhibited small irritation to the skin. In addition, the TUNEL staining results in each group confirmed that the MNs did not cause apoptosis before and after drug loading.

Example 5 Efficacy Experiment

Previous studies have shown that the production and release of IL-10 is the first and most important event in gout inflammation. TNF-α can enhance an activity of neutrophils. The proinflammatory cytokine IL-6 is a key to initiating the innate immunity. The contact of a synovial fluid with MSU crystals can lead to cell necrosis, macrophage release, neutrophil death, and inflammation. The COL-MN in Example 1 was applied to or a COL tablet solution (namely, COL) was intragastrically administered to the swollen skin of paws and ankles of rats induced by MSU crystals in each group. A therapeutic effect was evaluated based on inflammatory responses such as a paw swelling volume, inflammatory factor levels, plasma extravasation, and an MPO activity. COL-MN directly down-regulated the production of ROS by macrophages and inhibited the chemotaxis of neutrophils, thereby inhibiting the lens-induced inflammatory responses.

5.1 Animals 6-8-week-old male SD rats (body weight: 180 g to 200 g) were provided by the Animal Experiment Center of Anhui University of Chinese Medicine. All animal experiments were approved by the Ethics Committee of Anhui University of Chinese Medicine, with an animal ethics number: AHUCM-rats-2019001. The rats were raised in animal facilities under standardized conditions. The rats were fasted without water deprivation 12 h before the experiment.

5.2 Construction of an Acute Gout Rat Model Induced by MSU Crystals

MSU crystals were suspended in sterile saline to obtain an MSU suspension. An ankle was disinfected with 70% alcohol before surgery. Rats were divided into a saline group and an MSU group, with 6 rats in each group. Before MSU was injected, a horizontal line was drawn with an indelible marker at a position 5 mm above an ankle joint to unify a measurement standard for toe volumes. Then, a 21-gauge needle with 0.2 mL of the MSU suspension (25 mg/mL) was inserted into a tibialis anterior tendon of a rat at an inner side with a needle tip inclined at 45°, and the MSU suspension was injected into an ankle joint of the rat. The control group was injected with 0.2 mL of saline. Then, a toe volume of a rat was measured with a toe volume-measuring instrument.

Figure 9A:
FIGS. 9A-9F show the swelling and inflammatory cytokine levels of ankle joints in rats, where
Figure 9B:
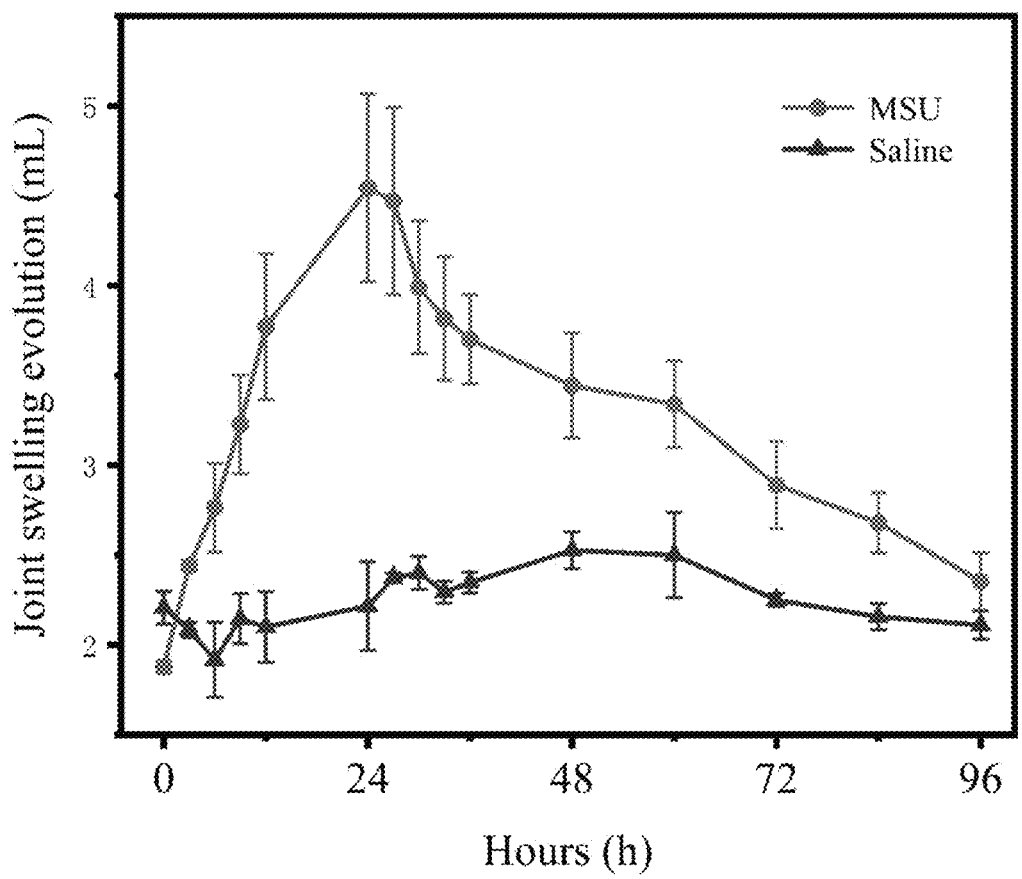

As shown in FIGS. 9A-9B, the in vivo pharmacodynamics of COL MN was evaluated by a rate model with AGA induced through the injection of MSU into an ankle joint cavity to observe an anti-inflammatory effect of the COL MN, and the anti-inflammatory effect of the COL MN was compared with an anti-inflammatory effect of saline. 24 h later, compared with saline-treated rats, ankle joints of MSU-treated rats were significantly swollen and the crawling of the MSU-treated rats was limited (FIG. 9A). Ankle joints of rats in the MSU group were extensively swollen, where the swelling occurred at 3 h after MSU injection, the swelling peaked at 24 h after MSU injection, and the swelling proceeded until 96 h after MSU injection (FIG. 9B).

5.3 Inhibition of COL MN on the Progression of Acute Gout in Rats

Data was analyzed with the SPSS software (version 26). Data was expressed as "mean standard deviation". The unpaired t-test was adopted for numerical variables between the two groups. The multiple comparisons were conducted with one-way analysis of variance (ANOVA) in combination with Bonferroni correction. *$P<0.05$, $P<0.01$, and *$P<0.001$ indicated statistical differences.

5.3.1 Grouping, Modeling, and Administration of Rats

Rats were randomly divided into the following 4 groups: 1) a blank group, 2) a model group, 3) a COL hydrogel MN group, and 4) a COL tablet solution (i.e. COL) group, with 10 rats in each group. Rats in the groups other than the blank group were modeled into acute gout models. 2 h later, COL-MN including 1 mg of COL was applied to ankles of rats in the COL-MN group, and fixed with a medical adhesive tape. Rats in the i.g. COL group were administered with a COL tablet (1 mg/mL) aqueous solution at 0.5 mg/kg.

5.3.2 Toe Volume Measurement

An initial toe volume of a rat was measured with a toe volume-measuring instrument. 24 h later, a toe volume of a rat in each group was measured.

Figure 9C:
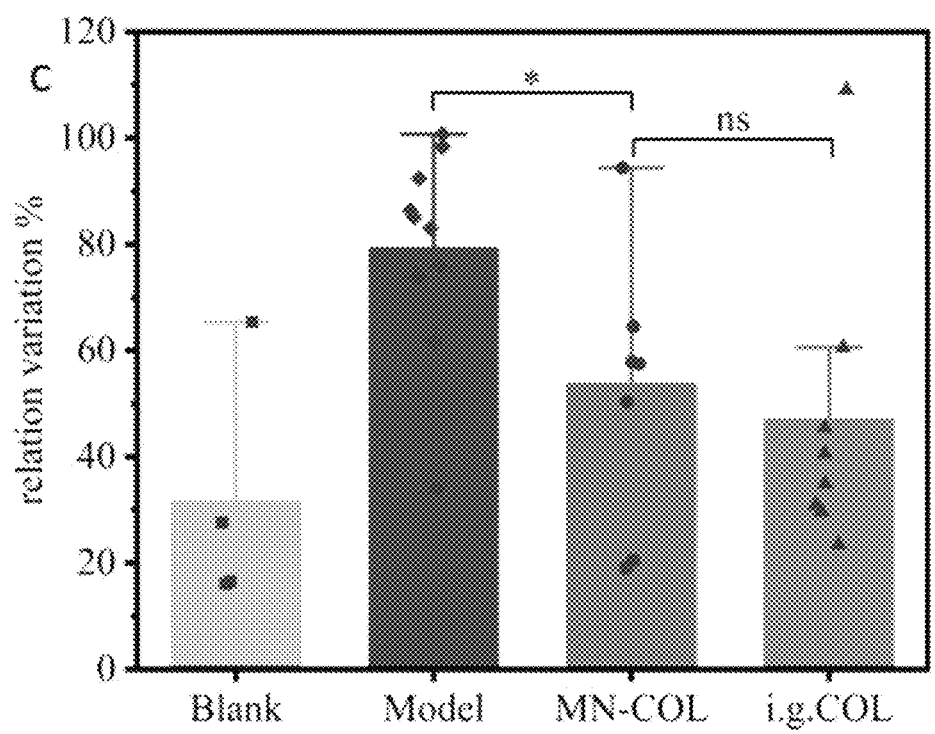

At the end of a treatment, a paw swelling volume of rats in the model control group increased by 80%. In contrast, after a treatment with COL-MN or i.g. COL, a change of a paw swelling volume increased to about 50%, and the paw swelling volume gradually decreased to 37% or less of a thickness of the model group (FIG. 9C).

5.3.3 Determination of Levels of Inflammatory Factors Such as IL-1β, TNF-α, and IL-6

The abdominal aortic blood was collected from rats, allowed to stand for 2 h, and centrifuged to obtain serum in an upper layer, and the serum was collected and stored at −80° C. The levels of inflammatory factors such as IL-1β, TNF-α, and IL-6 in the four groups were analyzed and determined with an enzyme-linked immunosorbent assay (ELISA) kit according to the instructions of a manufacturer. An absorbance value (OD) was measured with a microplate reader.

Figure 9D:
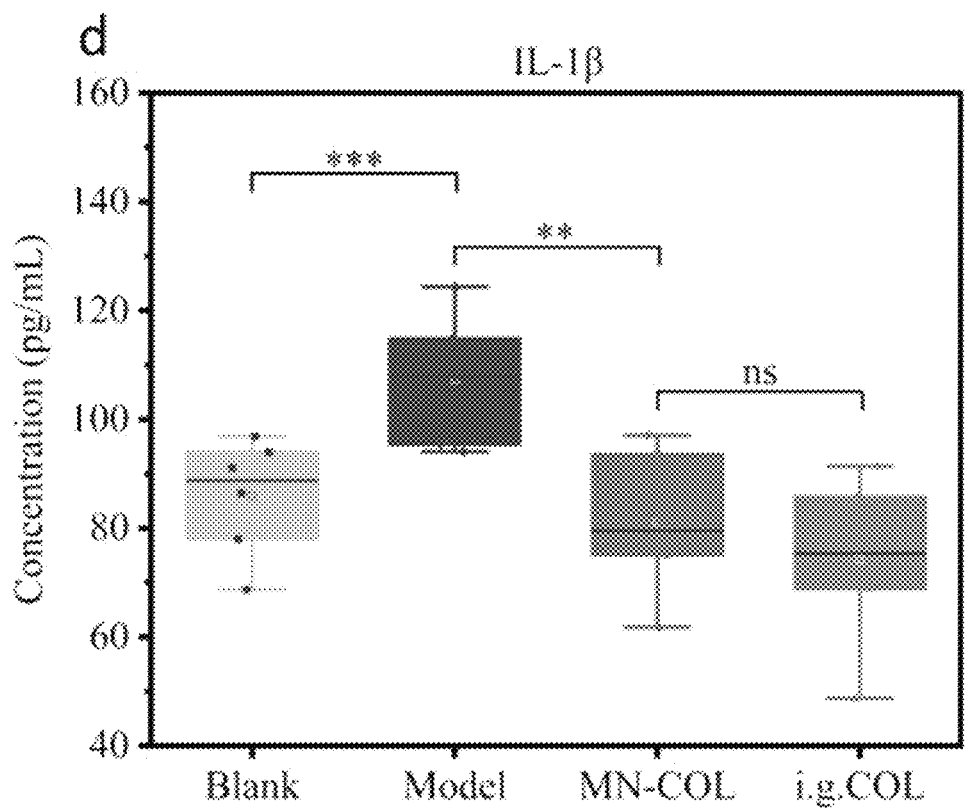
Figure 9E:
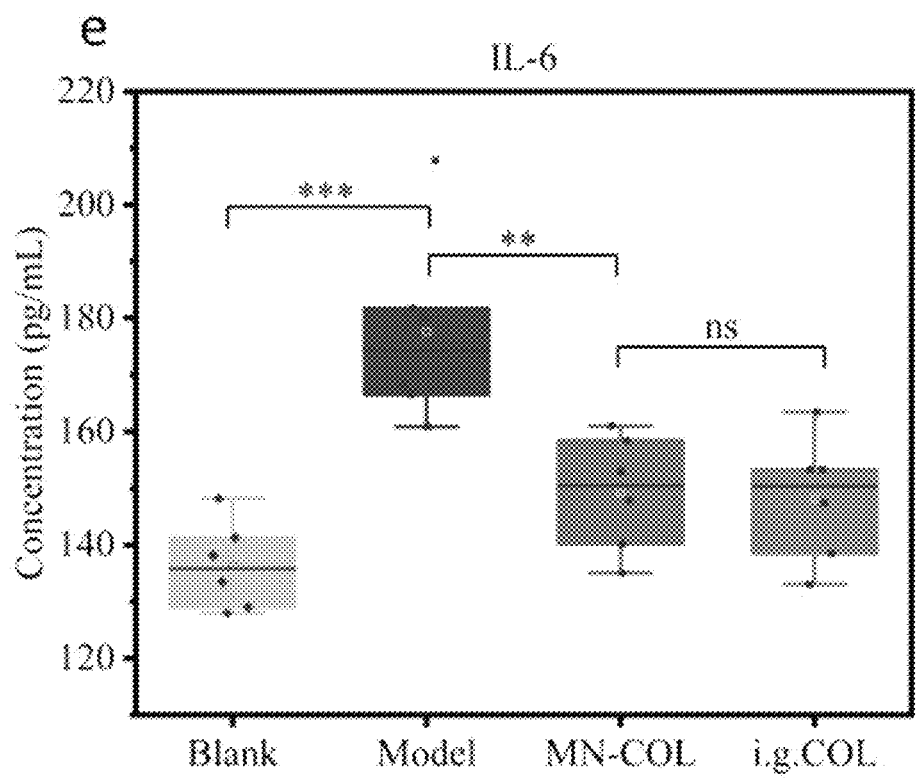
Figure 9F:
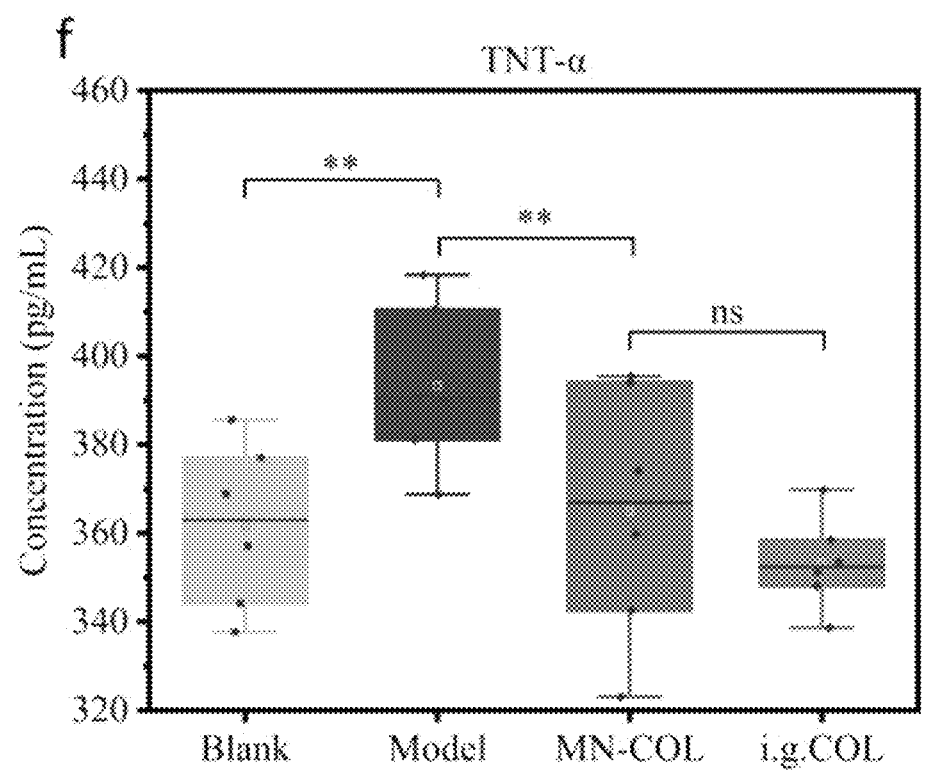

Compared with the model group, the levels of inflammatory factors IL-10, IL-6, and TNF-α in the serum of rats treated with COL-MN and i.g. COL decreased (FIGS. 9D-9F).

5.3.4 Detection of Plasma Extravasation at Ankle Joints of Rats

Figure 10A:
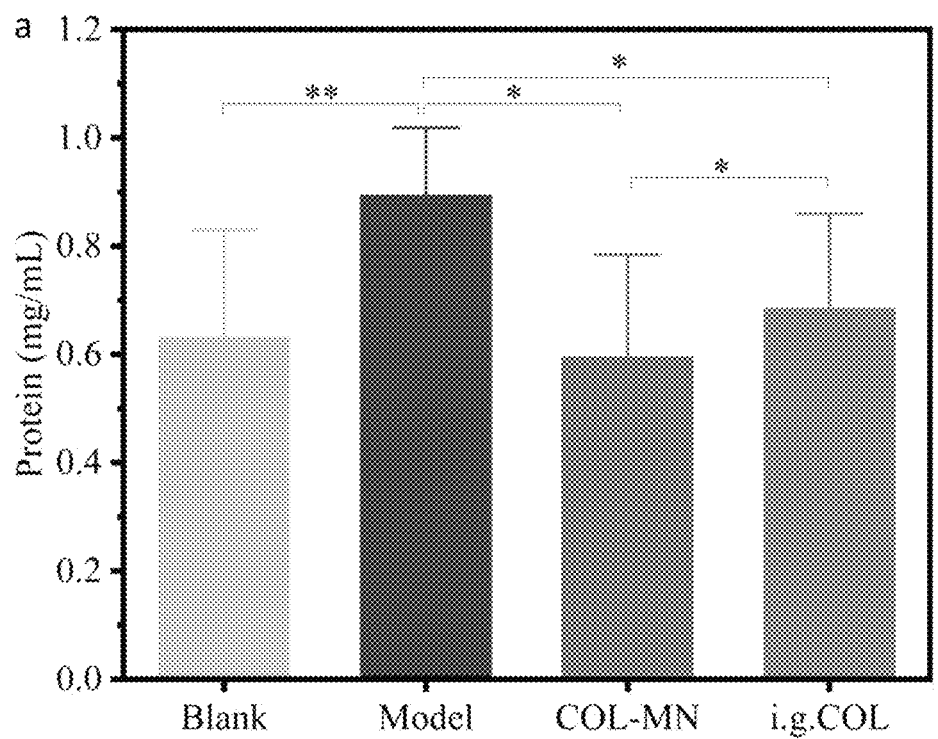
FIGS. 10A-10B show the responses of plasma extravasation (FIG. 10A) and myeloperoxidase (MPO) activity (FIG. 10B) after a COL-MN treatment (n=6).

An injected synovial cavity of an ankle joint was rinsed with 30 μL (3 times, with 10 μL for each time) of PBS to obtain a synovial lavage sample. With bovine serum albumin (BSA) as a standard, a total protein content was determined by the Bradford (1976) colorimetric method. 24 h after MSU injection, the plasma extravasation was caused by inflammation, and the plasma extravasation could be inhibited by COL-MN and i.g. COL to some extent (FIG. 10A).

5.3.5 Detection of Neutrophils in Ankle Joints of Rats

The presence of neutrophils in a synovial lavage fluid was evaluated by measuring an MPO activity. An ankle joint was weighed, chopped, and homogenized. An MPO activity in each group was detected with an MPO assay kit.

Figure 10B:
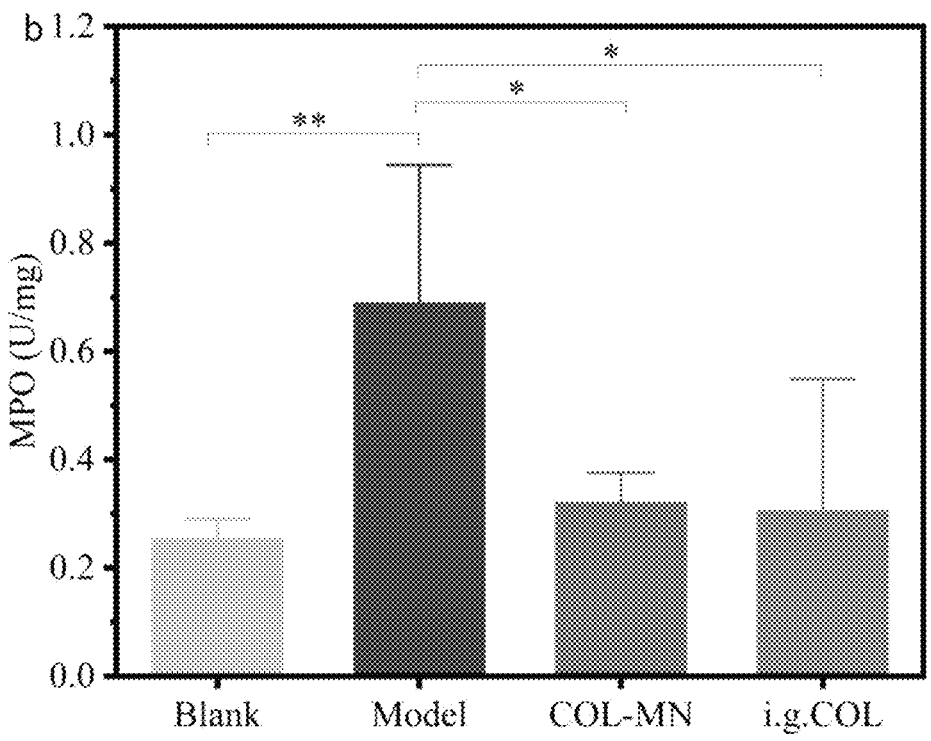

24 h after MSU injection, neutrophils were produced at an ankle joint, and the neutrophils could be inhibited by COL-MN and i.g. COL to some extent (FIG. 10B).

In summary, the MN and COL-MN prepared by the present disclosure have a complete needle shape, a neat matrix arrangement, cross-linking points evenly distributed in a network, and excellent mechanical properties and swelling performance. A drug load of COL-MN can reach an effectively-therapeutic dose, and the transdermal diffusion allows a sustained-release effect. COL-MN can exert a prominent anti-inflammatory effect through transdermal administration, and can effectively treat acute gout in rats that is induced by MSU crystals. Therefore, the present disclosure provides a new idea and strategy for the development and treatment of novel therapeutic dosage forms of COL.

What is claimed is:

1. A preparation method of a colchicine hydrogel microneedle, comprising the following steps:
    (1) dissolving acrylamide, N,N'-bis(acryloyl) cysteamine, and Irgacure 2959 in ultrapure water to obtain a gel solution, wherein mass proportions of the acrylamide, the N,N'-bis(acryloyl) cysteamine, and the Irgacure 2959 in the gel solution are 10 wt % to 35 wt %, 0.01 wt % to 1 wt %, and 0.01 wt % to 0.2 wt %, respectively;
    (2) pouring the gel solution into a polydimethylsiloxane (PDMS) mold, conducting a low-speed centrifugation, and conducting an ultrasonic treatment to eliminate air bubbles;
    (3) irradiating the PDMS mold with the gel solution under an ultraviolet light, and air-drying in an oven to obtain a hydrogel microneedle; and
    (4) adding a colchicine solution to the hydrogel microneedle, allowing swelling, air-drying, and demolding to obtain the colchicine hydrogel microneedle.

2. The preparation method of the colchicine hydrogel microneedle according to claim 1, wherein in the step (2), the low-speed centrifugation is conducted at 3,000 rpm to 4,000 rpm for 5 min to 20 min.

3. The preparation method of the colchicine hydrogel microneedle according to claim 1, wherein in the step (3), the irradiating under the ultraviolet light is conducted for 10 min to 60 min at 315 nm to 400 nm and 100 W to 500 W.

4. A colchicine hydrogel microneedle prepared by the preparation method according to claim 1.

5. The colchicine hydrogel microneedle according to claim 4, wherein in the step (2) of the preparation method, the low-speed centrifugation is conducted at 3,000 rpm to 4,000 rpm for 5 min to 20 min.

6. The colchicine hydrogel microneedle according to claim 4, wherein in the step (3) of the preparation method, the irradiating under the ultraviolet light is conducted for 10 min to 60 min at 315 nm to 400 nm and 100 W to 500 W.

* * * * *